(12) United States Patent
Nielsen

(10) Patent No.: US 7,892,583 B2
(45) Date of Patent: Feb. 22, 2011

(54) INITIATION OF FERMENTATION

(75) Inventor: Jan Clair Nielsen, Hundested (DK)

(73) Assignee: CHR. Hansen A/S, Horsholm (DK)

(*) Notice: Subject to any disclaimer, the term of this patent is extended or adjusted under 35 U.S.C. 154(b) by 976 days.

(21) Appl. No.: 10/562,421

(22) PCT Filed: Jun. 25, 2004

(86) PCT No.: PCT/DK2004/000455

§ 371 (c)(1), (2), (4) Date: May 17, 2006

(87) PCT Pub. No.: WO2004/113488

PCT Pub. Date: Dec. 29, 2004

(65) Prior Publication Data

US 2007/0009631 A1    Jan. 11, 2007

Related U.S. Application Data

(60) Provisional application No. 60/483,139, filed on Jun. 30, 2003.

(30) Foreign Application Priority Data

Jun. 26, 2003 (DK) .............................. 2003 00977

(51) Int. Cl.
C12G 1/022 (2006.01)
C12N 15/01 (2006.01)
C12N 1/20 (2006.01)

(52) U.S. Cl. .................. 426/15; 426/51; 435/252.1; 435/252.9; 435/440

(58) Field of Classification Search .................. None
See application file for complete search history.

(56) References Cited

U.S. PATENT DOCUMENTS

| 4,562,077 | A | 12/1985 | King et al. |
| 5,077,060 | A | 12/1991 | Prahl et al. |
| 5,460,837 | A | 10/1995 | D'Amico et al. |
| 5,607,854 | A | 3/1997 | Prahl et al. |
| 6,284,518 | B1 | 9/2001 | Henick-Kling et al. |

FOREIGN PATENT DOCUMENTS

EP      0 327 380      8/1989

OTHER PUBLICATIONS

Jan Clair Nielsen et al., "Malolactic fermentation in wine by direct inoculation with freeze-dried *Leuconostoc oenos* cultures", *American Journal of Enology and Viticulture*, vol. 47, No. 1, pp. 42-48, 1996.

Jan Clair Nielsen et al., "Control of flavor development in wine during and after malolactic fermentation by *Oenococcus oeni*", *Applied and Environmental Microbiology*, vol. 65(2) pp. 740-745, 1999.

S. K. Viljakainen et al., "The use of malolactic *Oenoccoccus oeni* (ATCC 39401) for deacidification of media containing glucose, malic acid and citric acid", *European Food Research and Technology*, Springer Verlag, Heidelberg, vol. 211, No. 6, pp. 438-442, 2000.

C. Carrie et al., "Comparison of Commercial Preparations of Lactic Acid Bacteria for Direct inoculation, for Control of Malolactic Fermentation of Merlot Wines", *Revue des Oenologues et des Techniques Vitivinicoles et oenologiques*, Union Nationale des Oenologues France Bourgogne-Publications, No. 103, pp. 16-18, 2002.

C. Reguant et al., "Influence of phenolic compounds on the physiology of *Oenococcus oeni* from wine", *Journal of Applied Microbiology*, vol. 88 (6), pp. 1065-1071, 2000.

Sibylle A. Krieger, "The use of active dry malolactic starter cultures", *Australian and New Zealand Wine Industry Journal*, vol. 8, No. 1, pp. 56-62, Feb. 1993.

A. Joyeux et al., "Comparison de diverses preparations industrielles de bacteries lactiques reactivees pour stimuler la fermentation malolactique", *Connaissance de la Vigne et du Vin*, Vigne et Vin Publications Internationales, vol. 19, No. 3, pp. 149-159, 1985.

H. D. Belitz et al., "Lehrbuch der Lebensmittelchemie", *Springer*, p. 767, Table 18.35, 1992.

E. Pilatte et al., "Development of a specific activator for malolactic bacteria", *Revue des Oenologues et des Techniques Vitivinicoles et oenologiques*, pp. 31-32, 1999.

B. W. Zoecklein et al., "Wine Analysis and Production", *Microbiology of Winemaking*, p. 296.

Barredo, *Microbial Processes and Products*, (Humana Press) p. 2, 2005.

(Continued)

Primary Examiner—N. M Minnifield
Assistant Examiner—Brian J Gangle
(74) Attorney, Agent, or Firm—Iver P. Cooper

(57) ABSTRACT

The present invention discloses microbial organisms capable of fermenting malic acid to lactic acid having impaired capability of degrading citric acid. These microbial organisms are for example useful in methods of preferentially degrading malic acid over citric acid in a liquid composition or in methods of inducing malolactic fermentation during wine production. The invention also discloses a concentrate of these microbial organisms and methods of preparing such a concentrate. The present invention furthermore relates to an activation solution useful for incubation of microbial organisms prior to inoculation into a liquid composition, such as wine.

71 Claims, 15 Drawing Sheets

OTHER PUBLICATIONS

Figure 1:
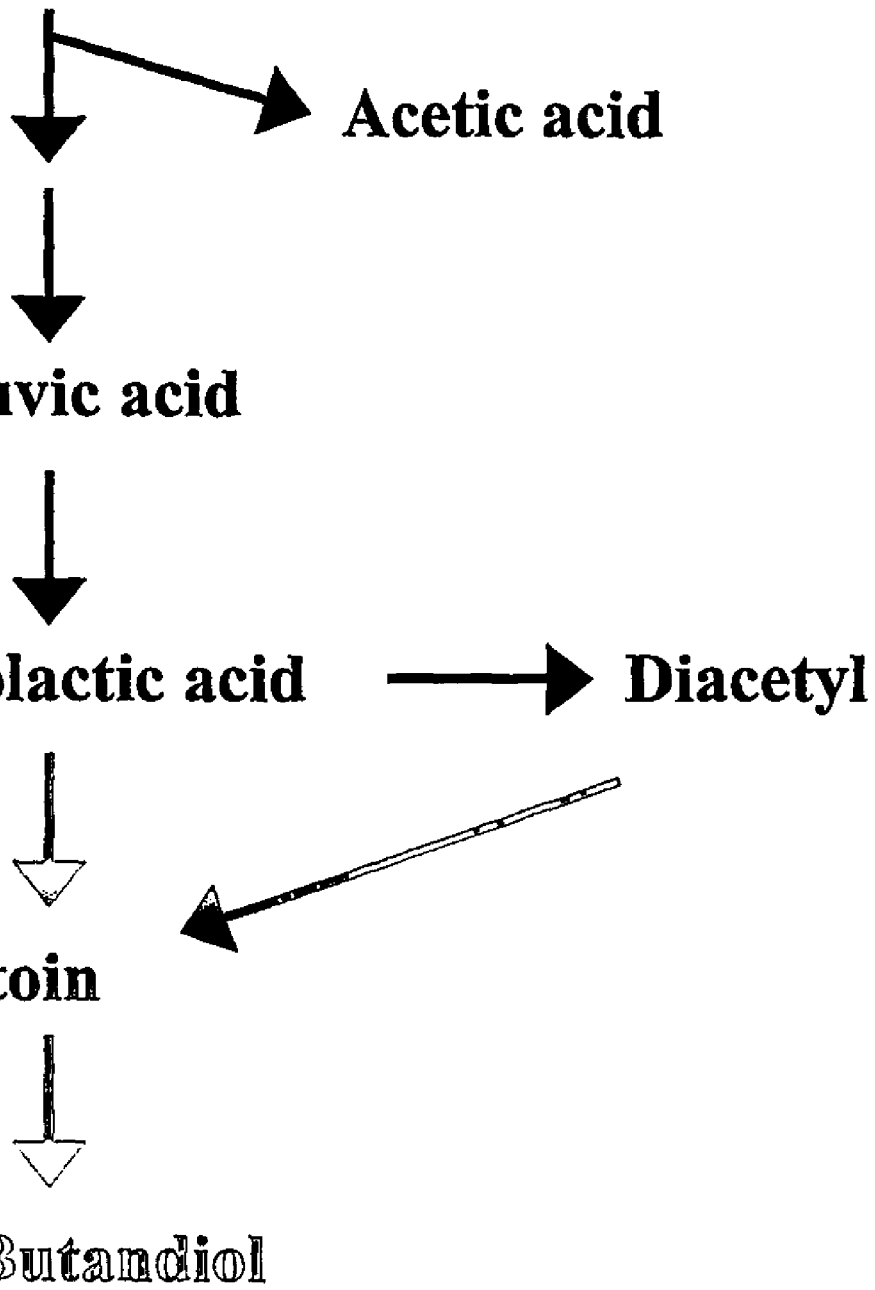

Buchanan, "Part 14. Gram-Positive Cocci", *Bergey's Manual of Determinative Bacteriology*, (The Williams & Wilkins Company/Baltimore) pp. 510-513, 1974.

Dicks, et al., "Proposal to Reclassify *Leuconostoc oenos* as *Oenococcus oeni* [corrig.] gen. nov., comb. nov.", *International Journal of Systematic Bacteriology*, vol. 45, No. 2, pp. 395-397, Apr. 1995.

Groisillier, et al., "Comparison of partial malolactic enzyme gene sequences for phylogenetic analysis of some lactic acid bacteria species and relationships with the malic enzyme", *International Journal of Systematic Bacteriology*, vol. 49, pp. 1417-1428, 1999.

Hawley, *The Condensed Chemical Dictionary*, (Van Nostrand Reinhold Company) pp. 224, 584, 805, 1977.

Lechiancole, et al., Abstract only, "Evaluation of intra-specific diversities in *Oenoccus oeni* through analysis of genomic and expressed DNA", *Systematic and Applied Microbiology*, vol. 29, issue 5, pp. 375-381, Jul. 2006.

Marcobal, et al., "Role of Hypermutability in the Evolution of the Genus *Oenococcus*", *Journal of Bacteriology*, vol. 190, No. 2, pp. 564-570, Jan. 2008.

"Concentration scales", *McGraw-Hill Encyclopedia of Science & Technology*, (McGraw-Hill) 9$^{th}$ Edition, pp. 584-585, 2002.

Mills, et al., Abstract only, "Genomic analysis of *Oenococcus oeni* PUSU-1 and its relevance to winemaking", *FEMS Microbiol. Rev.*, vol. 29(3), pp. 465-475, Aug. 2005.

de las Rivas, et al., Abstract only, "Allelic Diversity and Population Structure in *Oenococcus oeni* as Determined from Sequence Analysis of Housekeeping Genes", *Applied and Environmental Microbiology*, vol. 70, No. 12, pp. 7210-7219, Dec. 2004.

Van Harten, "History of mutation breeding", *Mutation Breeding Theory and Practical Applications*, (Cambridge U. Press), pp. 45-47, 51-56, 58-61, 2007.

Zé-Zé, et al., "The *Oenococcus oeni* genome: physical and genetic mapping of strain GM and comparison with the genome of a 'divergent' strain, PSU-1", *Microbiology*, vol. 146, pp. 3195-3204, 2000.

Fig. 11

Table 1

| Sample name | Cultivation time at sampling (hours) | OD 600 nm in sample | Sugar concentration in sample (g/l) | Calculated amount sugar fermented (g/l) |
|---|---|---|---|---|
| A | 27 | 2.0 | 64.2 | 44.8 |
| B | 35 | 2.9 | 42 | 68 |
| C | 40 | 3.3 | 26 | 84 |
| D | 45 | 3.5 | 10 | 100 |

Fig. 12

Table 2

| Sample name | % survival of inoculum measured day 2 in the wine |
|---|---|
| A | 0.4 |
| B | 10.2 |
| C | 44.0 |
| D | 98.0 |

Fig. 13

Table 3

| Sample name | Activation time at sampling (hours) | pH in sample | Sugar concentration in sample (g/L) | Calculated amount sugar fermented (g/L) |
|---|---|---|---|---|
| 1 | 4 | 4.02 | 54 | 46 |
| 2 | 8 | 3.77 | 35 | 65 |
| 3 | 19 | 3.62 | 28 | 72 |
| 4 | 46 | 3.43 | 15 | 85 |

Fig. 14

Table 4

| Sample name | % survival of inoculum mesured day 2 in the wine |
|---|---|
| 1 | 3% |
| 2 | 33% |
| 3 | 94% |
| 4 | 100% |
| Freeze dried | 1% |

INITIATION OF FERMENTATION

FIELD OF INVENTION

The present invention relates to methods and compositions for initiation of as well as to methods of fermentation in a liquid composition comprising a fermentable compound. In particular the invention relates to methods and compositions for initiation of malo-lactic fermentation during wine production.

BACKGROUND OF INVENTION

Wine contain L-malic acid in the range of 1 to 10 g/L. The amount of malic acid depends largely on the climatic conditions. Hence, wines produced in colder areas tend to have a relative higher concentration. From a taste and flavour point of view, malic acid is considered undesirable in most red wines and in several types of white wines and sparkling wines and from a practically/economically point of view malic acid is undesirable as it can support growth of bacteria in the wine after it has been bottled.

During the alcoholic fermentation only a small part of the present malic acid is degraded by the yeast. However, the content of malic acid in a wine may be effectively reduced by the so-called malolactic fermentation (MLF) which normally occurs after completion of the alcoholic fermentation. The MLF results from the catabolic activity of various lactic acid bacteria, including species belonging to the genera of *Lactobaccilus*, *Pediococcus* and *Oenococcus*.

The bacteria may be present in the wine as part of the indigenous microbial flora, or they may have been added as a bacterial starter culture. The most preferable bacteria species by winemakers is *Oenococcus oeni*, formerly known as *Leuconostoc oenos*. The catabolic phase is usually entered when the malolactically active bacteria during the growth phase has reached a population density of about $10^6$ colony forming units (CFU) per ml in the wine. During the MLF the bacteria degrade the malic acid, a dicarboxylic acid, to lactic acid, a monocarboxylic acid. As a result of this the acidity of the wine decreases and the pH increases, resulting in a wine with softer palate. Within the field the malolactic fermentation is considered completed when the concentration of malic acid in the wine is less than 30 mg/l (Zoecklein et al., in Wine Analysis and Production, Chapman and Hall, p 296).

However, during the malolactic fermentation *Oenococcus oeni* also degrade the citric acid, which normally is present in the wine at a concentration of 0.3-0.9 g/L. The catabolism of malic acid and citric acid is in general not concomitant, but sequential, i.e. the citric acid degradation is delayed compared to the malic acid fermentation (see for example Nielsen et al., 1999, Appl. Environ. Microbiol., 65:740-745 and Viljakainen and Laakso, 2000, Eur. Food Res. Technol., 211: 438-442). The degree of delay is dependent on the specific bacteria and the wine. The degradation of citric acid is often undesired as the wine looses some of its fruitiness which is appreciated in most wines. Another undesired and unavoidable effect of the citric acid degradation by *Oenococcus oeni* during MLF is the production of acetic acid, which is one of the end products from the citric acid degradation. The acetic acid concentration in the wine may increase with 0.1-0.3 g/L during the MLF. Acetic acid is highly undesired as it gives the wine an unpleasant vinegar flavour at higher concentration and the winemaker use much attention to keep the acetic acid concentration in the wine as low as possible during the different winemaking steps. Besides the lactic acid bacteria the other sources of acetic acid in winemaking is yeast and acetic acid bacteria. An important intermediary compound in the metabolism of citric acid by *Oenococcus oeni* is diacetyl. When present at concentration above the sensory threshold, diacetyl gives the wine a buttery aroma which is undesired in most red wines. However, in some white wines, e.g. Chardonnay the aroma may be appreciated.

Because the winemaker often prefer to exercise a greater degree of control over the malolactic fermentation process it has become increasingly common practice in the wine industry to induce the fermentation by use of commercially available concentrated frozen or freeze dried starter cultures of *Oenococcus oeni*, which are inoculated directly into the wine without any prior re-hydration and activation steps. The usefulness of a concentrated frozen or freeze dried culture which are inoculated direct into wine depends very much on the survival rate of the bacteria culture after the inoculation. The transition of the bacteria from a friendly propagation medium with high pH and high nutrition level to the hostile condition in wine with high ethanol concentration, low pH, low nutrition level, and presence of $SO_2$ is very stressful for the bacteria and may result in survival rates below 1% in the inoculated wine.

Typically, the described propagation medium for lactic acid bacteria, including *Oenococcus oeni*, contain various nutrients such as vitamins, minerals, yeast extract and sugars. The amount of sugars in the media are normally within 20-50 g/L as higher concentrations of sugars are considered to strongly reduce or inhibit the growth of lactic acid bacteria. In the prior art higher concentrations of sugars in the propagation medium have therefore been considered to be of no practically use or economically interest.

Freeze dried cultures of a strain of *Oenococcus oeni*, which do not ferment the citric acid in the wine during the malolactic fermentation, are commercially available. There are several advantages in using this strain for malolactic fermentation in wine. The fruitiness of the wine is conserved, there is no production of acetic acid during the malolactic fermentation and there is no production of the buttery flavour, diacetyl. However, the commercial cultures of this strain on the market can not be used for direct inoculation into wine as this results in a survival rate which is of no practical use. According to the commercial application manuals of the products the freeze dried cultures needs re-hydration and an adaptation procedure involving several steps before the bacteria can be inoculated into wine. The first step may involve dissolving the freeze dried product in 5 L of half water, half grape juice or wine added different nutrition. After 5-7 days incubation the pre-culture is diluted with 20-200 L wine which is incubated for another 2-12 days before the final inoculation into the production tank with wine. The adaptation steps are very time and labour consuming for the winemaker as he has to follow the adaptation steps carefully, and there is a high risk for contamination with spoilage bacteria and yeast as the adaptation steps under the practical conditions in the wineries can not be conducted under sterile conditions.

WO 9320180 discloses a method for inducing malolactic fermentation in wine or fruit juice by the direct inoculation of a concentrate of a starter culture containing a selected malolactically active bacteria strain having a survival rate of at least 80% when introduced into a wine having a pH of 3.2 or lower and containing at least 25 mg $SO_2$ per L and at least 12 vol % ethanol, and capable of starting malolactic fermentation when added directly to the wine or fruit juice at a concentration of less than $10^7$ colony forming units per ml. Said bacteria strain is also capable of degrading citric acid. The document clearly indicates that the bacteria strains ability to survive the direct inoculation into wine is linked to the genetic of the strain selected. According to the disclosure the selected bacteria strains are propagated according to processes which are well-known in the art.

U.S. Pat. No. 6,284,518 B1 discloses a media for propagation of different lactic acid bacteria species, including *Oenococcus oeni*. According to the disclosure a key feature of the invention is the use of a fructose/glucose mixture where fructose is the primary carbohydrate source. Fructose/glucose mixtures containing between 3% to about 45% glucose can be employed, preferably the amount is between 5% and about 40% glucose. Most preferable, the amount is less then 20% of the mixture. In the disclosed media, as biomass growth occurs, the pH is allowed to drop. The amount of carbohydrate source in the disclosed medium is between 30 g/L to 60 g/L. They document describes that $10^6$-$10^7$ bacteria/ml are inoculated into the medium and the bacteria are then propagated for 6-8 days before the bacteria can be inoculated into wine.

In U.S. Pat. No. 4,562,077 is disclosed a method for the reduction of malic acid to lactic acid in wine which comprises the inoculation of a culture concentrate into non-sterile fruit juice containing a nitrogen source to provide about $10^7$ to $10^{10}$ bacteria per ml. After this activation step the mixture of fruit juice and bacteria are introduced into wine or grape must to produce wine having a reduced malic acid content. The activation conditions disclosed are an activation period of 48 to 72 hours at 18° C. to 25° C.

Carrié et al., 2002, Revue des OEnologues 103: 16-18 describes various malic acid fermenting bacteria, some of which can be inoculated directly into wine. The document furthermore describes the citric acid concentration in wine after/during malolactic fermentation with these bacteria. It appears from FIG. 1 of the document that malolactic fermentation is completed for only one of the strains investigated (strain F). Thus, citric acid concentration is determined prior to or at completion of malolactic fermentation. Because citric acid fermentation is delayed compared to malic acid fermentation (see herein above), citric acid concentration is determined prior to completion of Citric acid degradation. The document is silent regarding whether the bacteria disclosed therein are capable of degrading citric acid. Because lactic acid bacteria normally are capable of degrading citric acid, it must be anticipated that the bacteria disclosed in the document are capable of degrading citric acid.

Nielsen et al., 1996 Am. J. Enol. Vitic. 47:42-48 describes *Leuconostoc oenos* bacterial cultures capable of fermenting malic acid to lactic acid. The bacteria can be inoculated directly into wine. The bacteria are capable of degrading citric acid.

Nielsen and Richelieu, 1999, Appl. Environ. Microbiol. 65:740-745 describes malolactic fermentation and describes that citric acid degradation is delayed compared to degradation of malic acid.

U.S. Pat. No. 5,460,837 describes a method of initiating malolactic fermentation by cultivating malolactically active bacteria in a medium comprising 0.05 to 0.5% glucose, separation of biomass and optionally freeze drying. The freeze dried cultures may be inoculated directly in wine.

SUMMARY OF INVENTION

It is therefore an object of the present invention to provide improved methods of inducing specific fermentation processes in a liquid composition.

Hence, in one aspect the present invention relates to induction of specific fermentation processes in a liquid composition comprising at least one fermentable compound as well as to microbial organisms for use in said methods.

In particular the present invention provides, compared to known methods, a significant improved method of inducing malolactic fermentation in wine or fruit juice without the concomitant degradation of citric acid, production of acetic acid, and production of diacetyl herein within a short period of time by inoculation wine or a fruit juice directly with a concentrated culture composition of malolactically active and non-citric acid fermenting bacteria at an economically feasible concentration and accordingly, to avoid the tediously, risky and costly processes of re-hydration, activation, and adaptation which are currently required with commercial malolactically non-citric acid fermenting starter cultures.

Also, the present invention provides, compared to known methods, a significant improved method of inducing malolactic fermentation in wine or fruit juice within a short period of time by inoculation wine or a fruit juice with a specially activated concentrated culture solution of malolactically active and citric acid or non-citric acid fermenting bacteria at an economically feasible concentration and accordingly, to avoid the lag and dead phase observed when commercial dry malolactic starter cultures are inoculated directly into wine and also to significantly improve the tediously, risky and costly processes of re-hydration, activation, and adaptation which are currently required with commercial malolactic starter cultures not suitable for direct inoculation into wine.

It is therefore a first objective of the present invention to provide isolated and purified microbial organisms, wherein said microbial organisms are capable of fermenting malic acid to lactic acid, and wherein said microbial organism when placed in a medium containing a predetermined amount of citric acid is only capable of degrading at the most 80% of said citric acid, and wherein the microbial organism has at least one of the following characteristics, when said microbial organism in a frozen or freeze dried state is added directly into a fermented fruit juice:

i) a survival rate which is at least 1% after two days at 23° C. in a fermented sterile fruit juice with a pH of less than 4 and comprising at least 12 vol % ethanol ii) a survival rate which is at least 70% after two days at 17° C. in a fermented sterile fruit juice with a pH of less than 4 comprising at least 13.9 vol % ethanol Hence, said microbial organism may be added directly into for example a fermented fruit juice during wine production without any previous adaptation. It is in general laborious to adapt bacteria to growth in fermented fruit juice and there is a high risk of contamination using the conventional adaption procedure, in particular in a normal winery where the adaptation frequently cannot be done under sterile conditions.

It is also an objective of the present invention to provide a concentrate comprising or consisting of said microbial organism(s), wherein said concentrate has a content of colony forming units being in the range of $10^9$ to $10^{12}$ per g.

It is a second objective of the present invention to provide methods of preferentially degrading malic acid over citric acid in a liquid composition comprising malic acid and citric acid, said methods comprising the steps of i) Providing a liquid composition comprising malic acid and citric acid;

ii) Providing a microbial organism capable of fermenting malic acid to lactic acid, wherein said microbial organism when placed in a medium containing a predetermined amount of citric acid is only capable of degrading at the most 80% of said citric acid, and wherein said microbial organism has been frozen or freeze dried, iii) Adding said freeze dried or frozen microbial organism directly to said liquid composition iv) incubating said liquid composition and said microbial organism under conditions which allow degradation of at least 70% of the malic acid, v) thereby obtaining a final liquid composition comprising less than 30% of the initial malic acid and at least 20% of the initial citric acid.

Preferably said microbial organism has at least one of the characteristics outlined herein above.

It is a third objective of the present invention to provide methods of inducing malolactic fermentation during wine production, comprising the steps of i) Providing a grape juice or a fermented grape juice ii) Providing a microbial organism capable of fermenting malic acid to lactic acid, wherein said microbial organism when placed in a medium containing a predetermined amount of citric acid is only capable of degrading at the most 80% of said citric acid, iii) Incubating said grape juice or fermented grape juice with said microbial organism under conditions which allow degradation of malic acid, iv) thereby inducing malolactic fermentation Preferably said microbial organism has at least one of the characteristics outlined herein above.

It is another objective of the present invention to provide methods of producing the microbial organism described herein above, wherein said method comprises the steps of i) Providing a microbial organism resistant to a pH below 5 and an ethanol concentration of at least 8%, ii) Subjecting said microbial organism to mutagenesis, thereby obtaining more than one different mutated microbial organism iii) Selecting mutated microbial organisms capable of fermenting malic acid to lactic acid, wherein said microbial organism when placed in a medium containing a predetermined amount of citric acid is only capable of degrading at the most 80% of said citric acid, and wherein the microbial organism has at least one of the following characteristics, when said microbial organism in a frozen or freeze dried state is added directly into a fermented fruit juice:

a) a survival rate which is at least 1% after two days at 23° C. in a fermented sterile fruit juice comprising at least 12 vol % ethanol;

b) a survival rate which is at least 70% after two days at 17° C. in a fermented sterile fruit juice comprising at least 13.9 vol % ethanol It is a further objective of the present invention to provide methods of preparing a freeze-dried microbial organism capable of fermenting malic acid to lactic acid, which has reduced citric acid degrading activity and which is capable of survival after direct inoculation into fermented fruit juice, said method comprising the steps of i) Providing a microbial organism capable of fermenting malic acid to lactic acid, wherein said microbial organism when placed in a medium containing a predetermined amount of citric acid is only capable of degrading at the most 80% of said citric acid, ii) Providing an adaptation medium comprising at least 6% sugar iii) Propagating said microbial organism in said adaptation medium under conditions allowing growth of said microbial organism iv) Harvesting said microbial organism v) Freeze-drying said microbial organism It is a still further objective of the present invention to provide an activation solution comprising i) A nitrogen source ii) In the range of 60 to 140 g sugar per L iii) In the range of $5 \times 10^8$ and $5 \times 10^{10}$ colony forming units per ml of a microbial organism capable of fermenting at least one fermentable compound Said activation solution is useful for adapting freeze-dried or frozen microbial organisms to growth in liquid solutions with a pH below 5 and/or an alcohol content above 10%. When using this adaptation solution, the adaptation procedure is much faster and easier to handle compared to conventional adaptation procedures.

It is an even further objective of the present invention to provide a dry activation composition, wherein in the range of 80 to 200 g of said dry activation composition comprises i) a nitrogen source ii) In the range of 60 to 140 g sugar iii) In the range of $5 \times 10^{11}$ and $5 \times 10^{13}$ colony forming units of a microbial organism capable of fermenting a fermentable compound, wherein addition of 1 L water to said dry activation compositions results in an activation solution as described above.

It is yet another objective of the present invention to provide methods of inducing fermentation in a liquid composition comprising a fermentable compound comprising the steps of i) Providing a dry activation composition as described herein above, wherein the composition comprises a microbial organism capable of fermenting said fermentable compound ii) Adding water to said dry composition, thereby obtaining an activation solution iii) Incubating said activation solution for an activation time under activation conditions iv) Providing a liquid composition comprising said fermentable compound v) Inoculating said liquid composition with said activation solution vi) Thereby inducing fermentation in said liquid composition

DESCRIPTION OF DRAWINGS AND TABLES

FIG. 1. Main pathways for the citric acid metabolism by *Oenococcus oeni*

Figure 2:
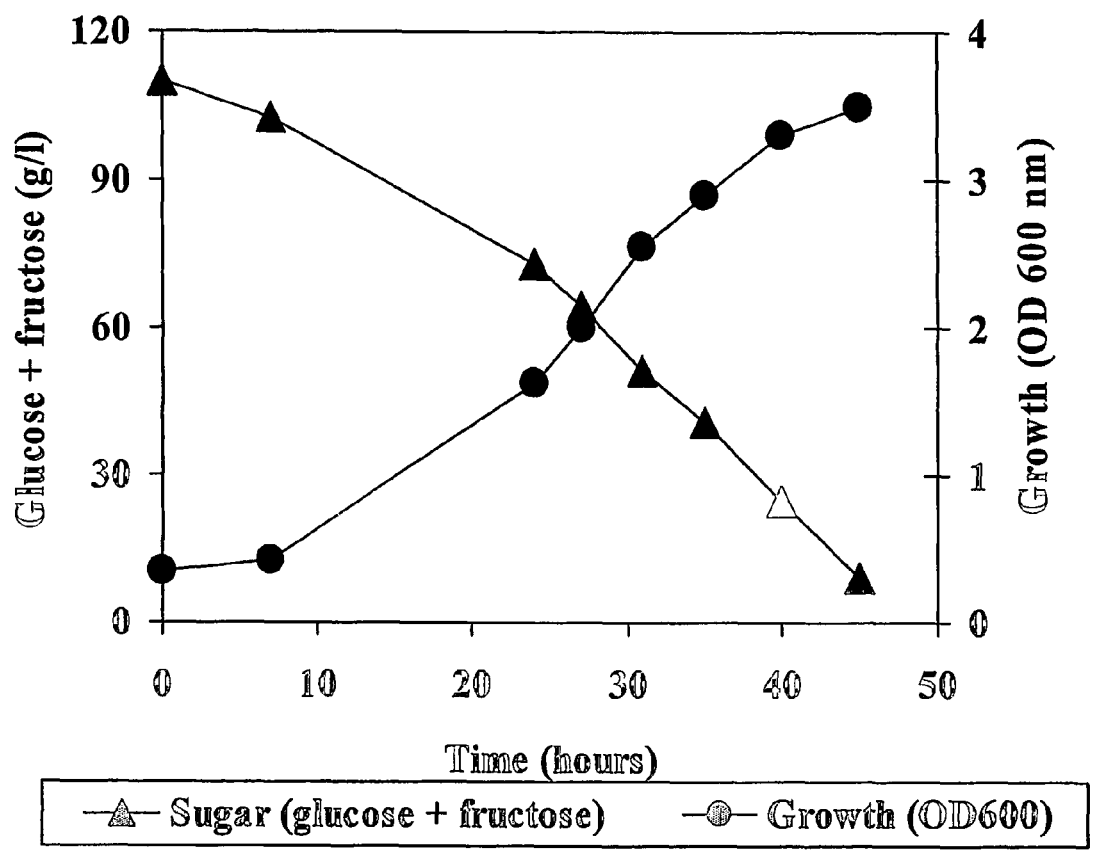

FIG. 2. Sugar concentration and growth of the selected non-citric acid fermenting mutant strain *Oenococcus oeni* DSM 15571 in the cultivation and adaptation medium as a function of time. The cultivation was conducted at constant pH 4.5 and 30° C.

Figure 3:
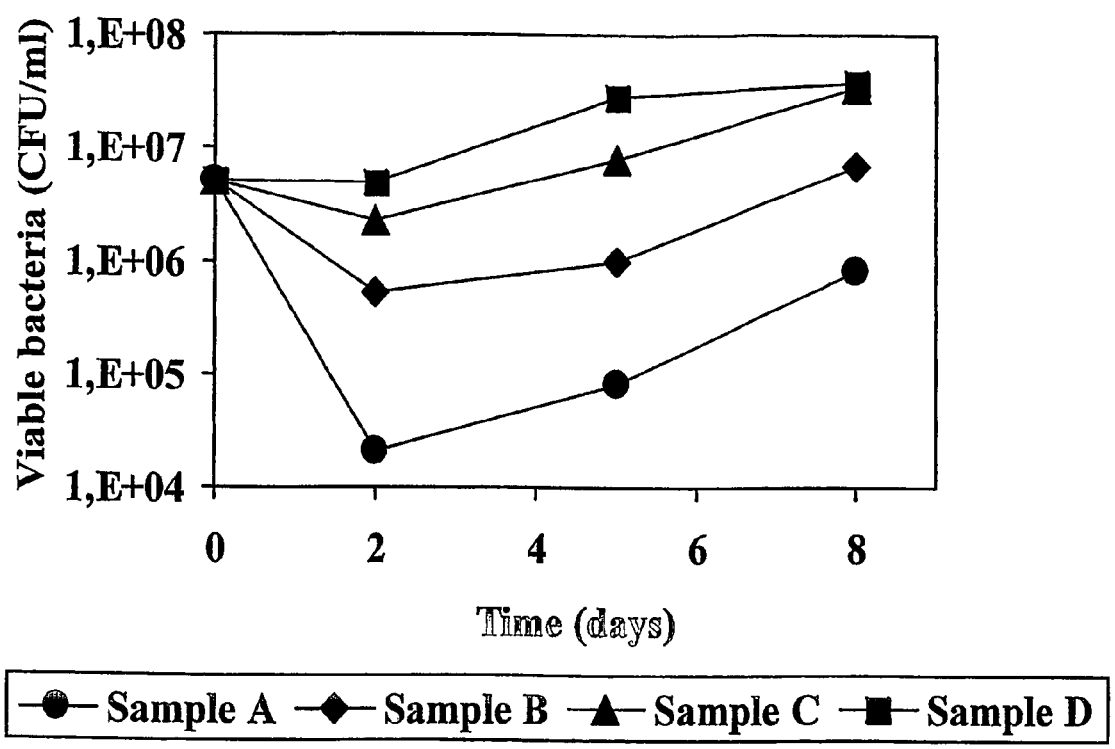

FIG. 3. Number of viable bacteria in experimental wine inoculated directly with freeze dried samples of the selected non-citric acid fermenting strain *Oenococcus oeni* DSM 15571 and kept at 23° C. The sample A, B, C, and D were harvested from the cultivation and adaptation medium after 27, 35, 40, and 45 hours respectively (FIG. 2), followed by concentration and freeze-drying before inoculation into the experimental wine.

Figure 4:
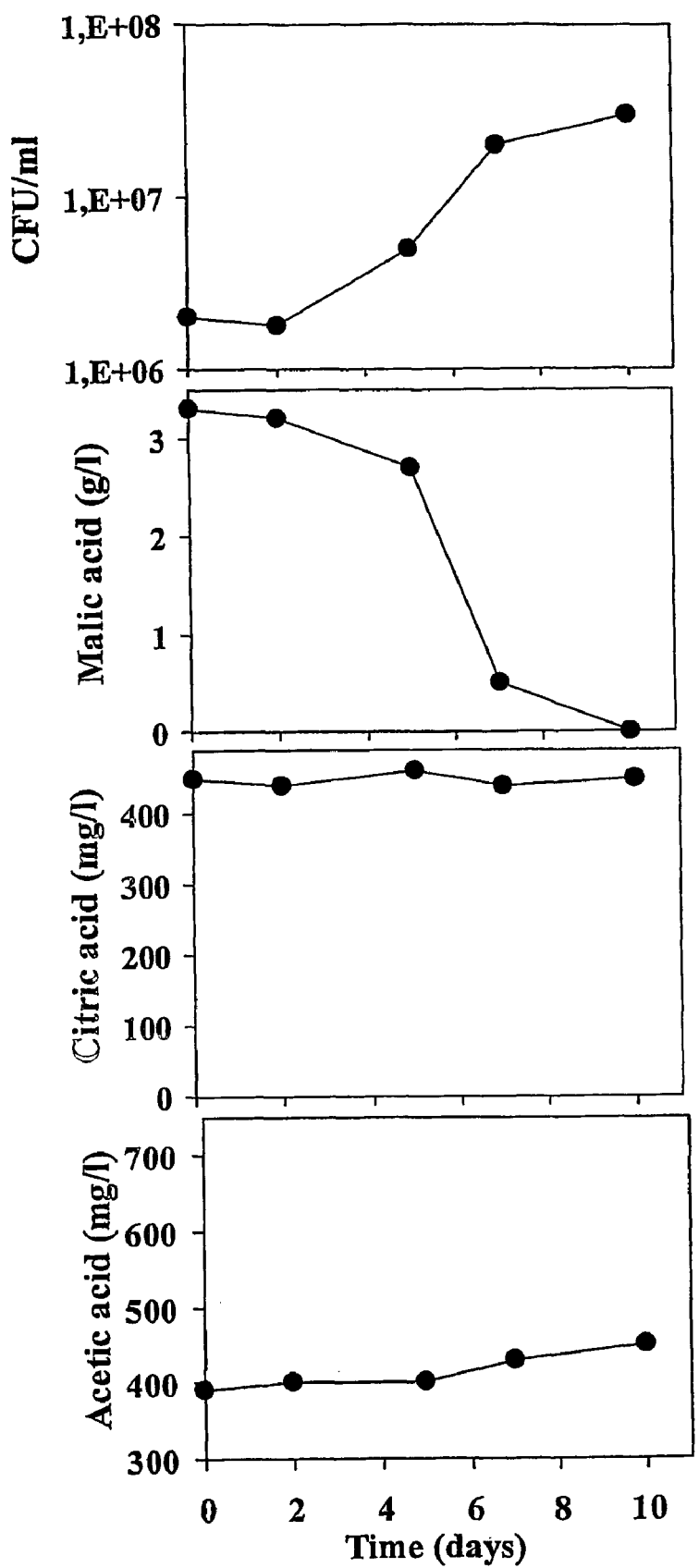

FIG. 4. Degradation of malic and citric acid, production of acetic acid, and CFU/ml of active bacteria in experimental wine after direct inoculation with freeze dried composition of the non-citric acid fermenting mutant strain *Oenococcus oeni* DSM 15571. The experiment was conducted at 23° C.

Figure 5:
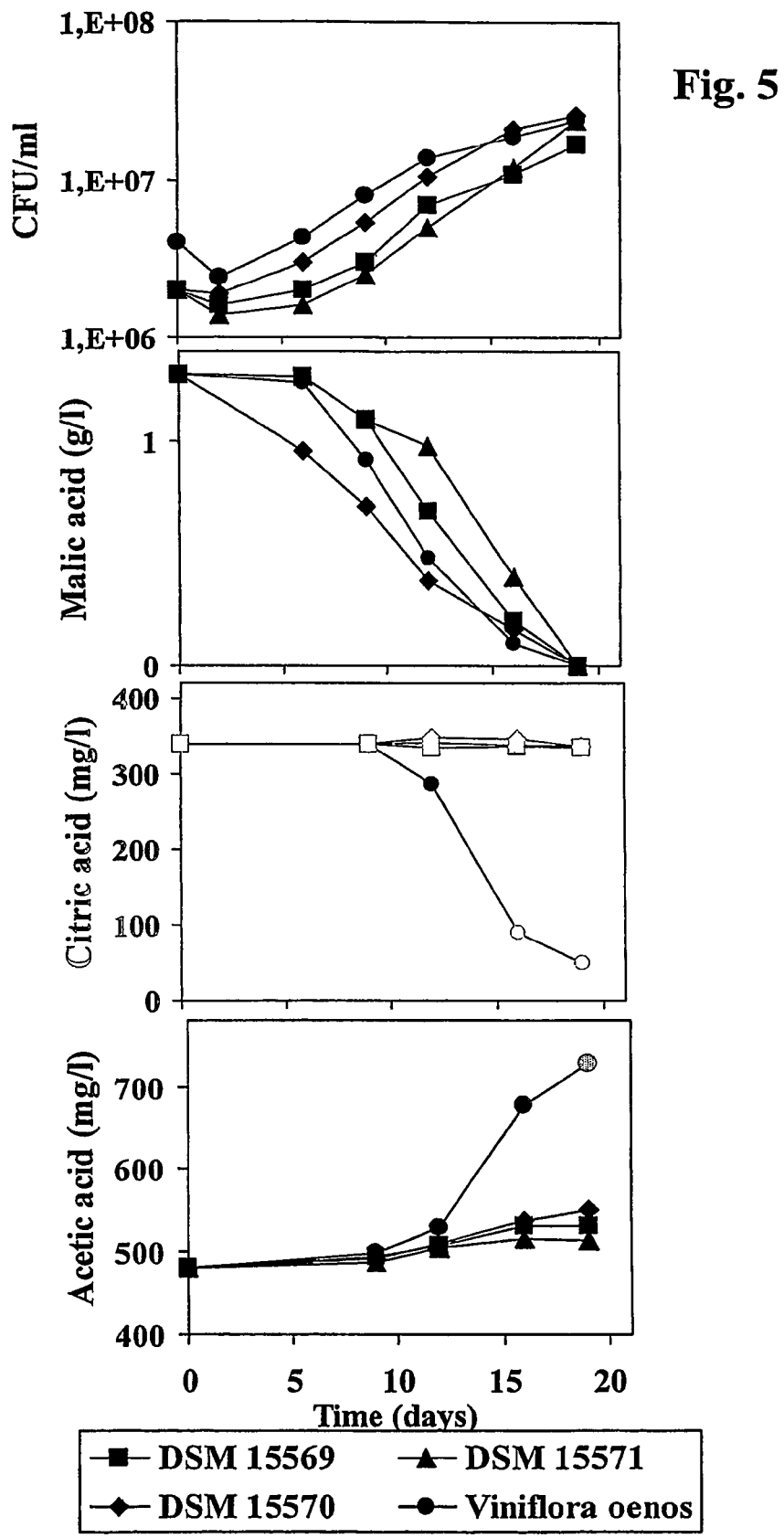

FIG. 5. Degradation of malic acid and citric acid, production of acetic acid, and CFU/ml of active bacteria in Pinot Noir wine (13.8 vol % ethanol, pH 3.54, 30 ppm $SO_2$ added at crush) from Russian River, Calif., after direct inoculation with freeze dried compositions of the selected non-citric acid fermenting *Oenococcus oeni* strain DSM 15570, strain DSM 15569, and strain DSM 15571. For comparison, the commercial product Viniflora oenos from Chr. Hansen A/S, Denmark, which contain a normal citric acid fermenting *Oenococcus oeni* strain (DSM 7008), was included in the experiment. The experiment was conducted in 250 L oak barrels at 18° C.

Figure 6A:
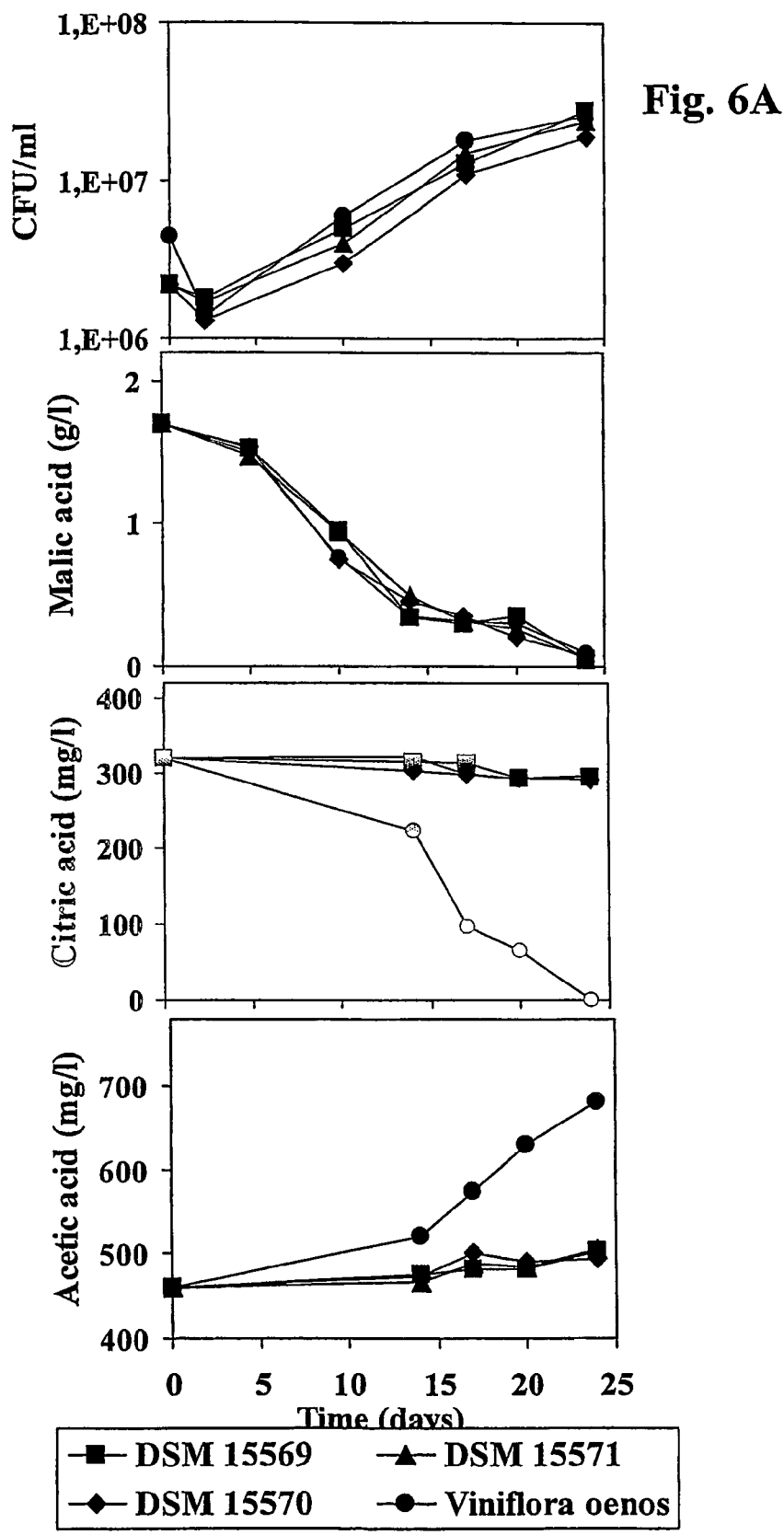

FIG. 6A. Degradation of malic acid and citric acid, production of acetic acid, and CFU/ml of active bacteria in Pinot Noir wine (13.9 vol % ethanol, pH 3.57, no $SO_2$ added at crush) from Sonoma, Calif., after direct inoculation with freeze dried composition of the non-citric acid fermenting *Oenococcus oeni* strain DSM 15570, strain DSM 15569, and strain DSM 15571. For comparison, the commercial freeze dried product Viniflora oenos from Chr. Hansen A/S, Denmark, which contain a normal citric acid fermenting *Oenococcus oeni* strain (DSM 7008), was included in the experiment. The experiment was conducted in 250 L oak barrels at 17° C.

Figure 6B:
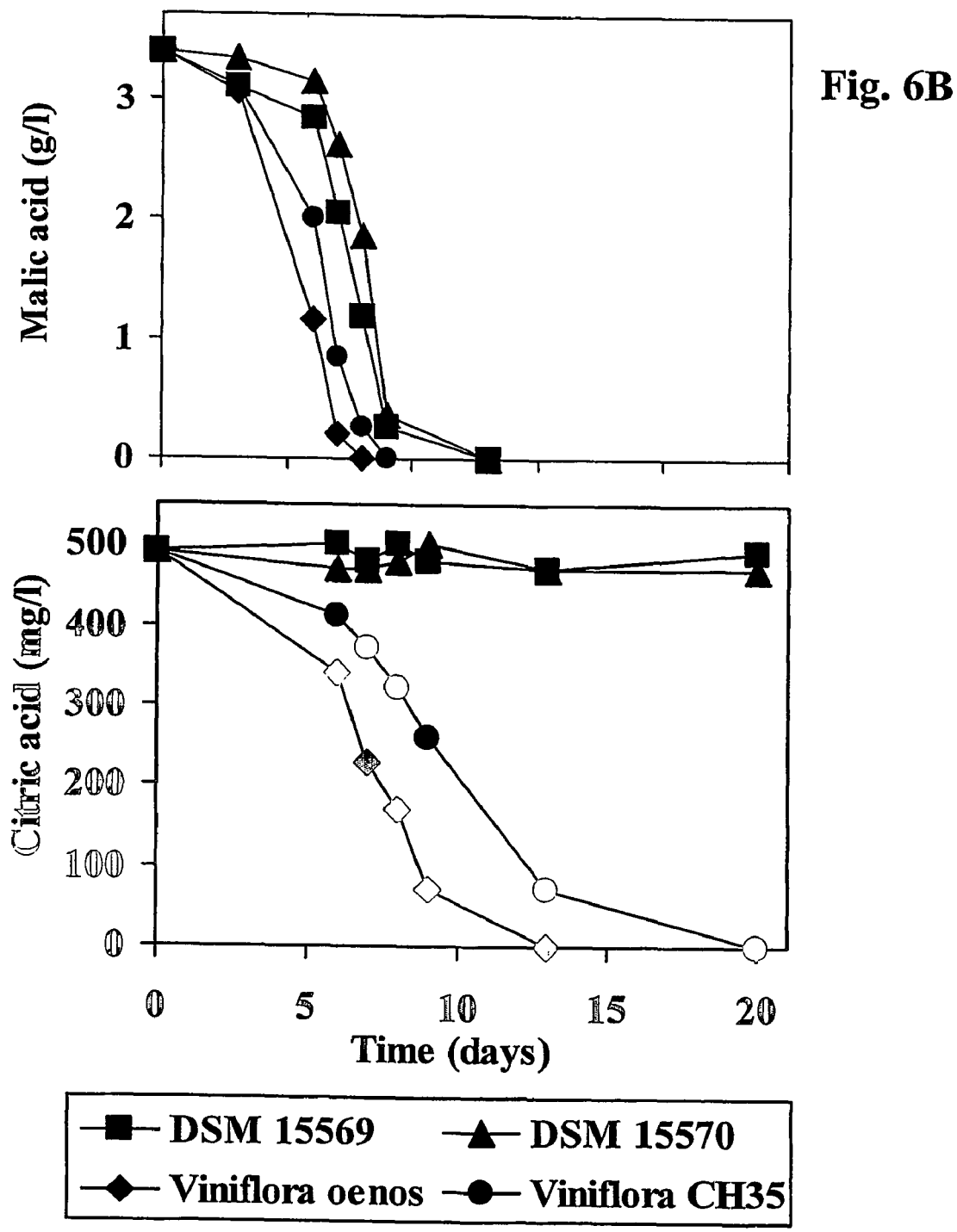

FIG. 6B. Degradation of malic and citric acid in experimental wine after direct inoculation with freeze dried composition of the non-citric acid fermenting mutant strains *Oenococcus oeni* DSM 15569 and DSM 15570. For comparison the commercial freeze dried products Viniflora oenos and Viniflora CH35 from Chr. Hansen A/S, Denmark, which contain normal citric acid fermenting *Oenococcus oeni* strains, were included in the experiment. The experiment was conducted at 23° C.

Figure 7:
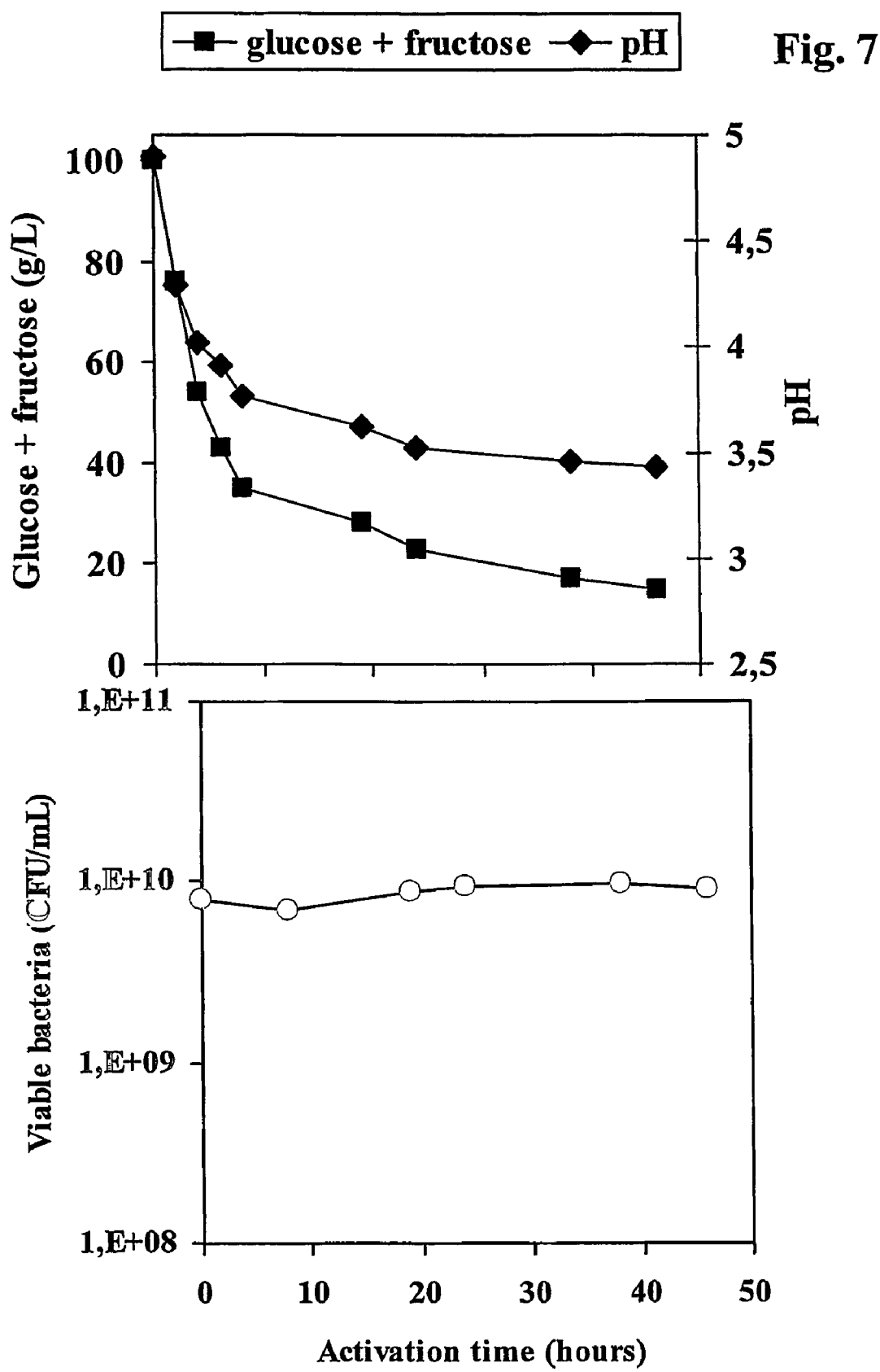

FIG. 7. Total glucose+fructose, pH, and number of viable bacteria of the normal citric acid fermenting *Oenococcus oeni* strain DSM 15568 as a function of time in the activation composition solution incubated at 23° C. The activation composition solution was prepared by the addition of water to the dry activation composition described in the text.

Figure 8:
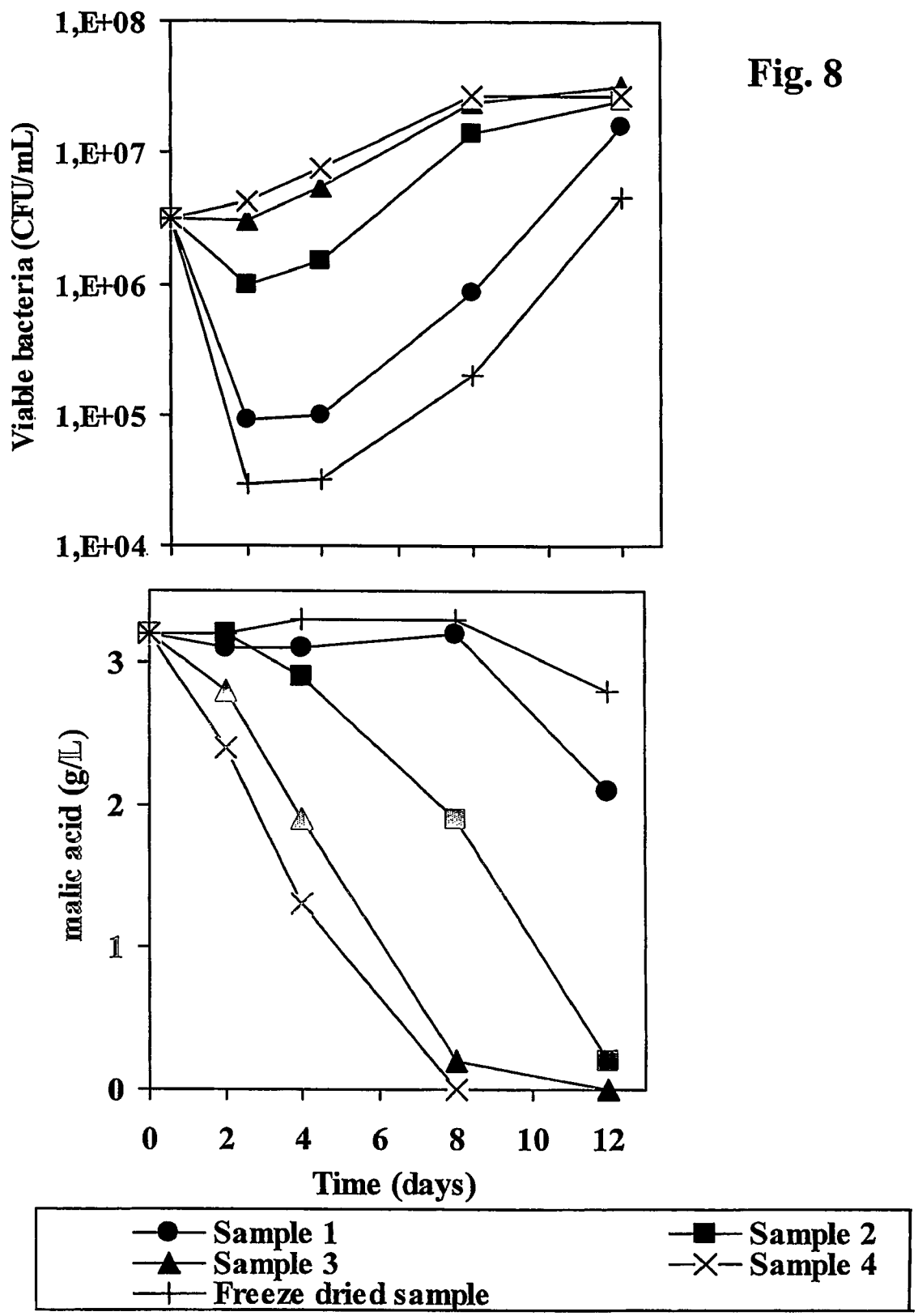

FIG. 8. Number of viable bacteria and malic acid concentration in the experimental wine inoculated with activated samples of the normal citric acid fermenting strain *Oenococcus oeni* DSM 15568 and kept at 23° C. The activated samples, named 1, 2, 3, and 4 were harvested from the bacteria activation composition solution after respectively 4, 8, 19 and 46 hours of activation (FIG. 7). Included in the experiment was also the direct inoculation of freeze dried *Oenococcus oeni* DSM 15568.

Figure 9:
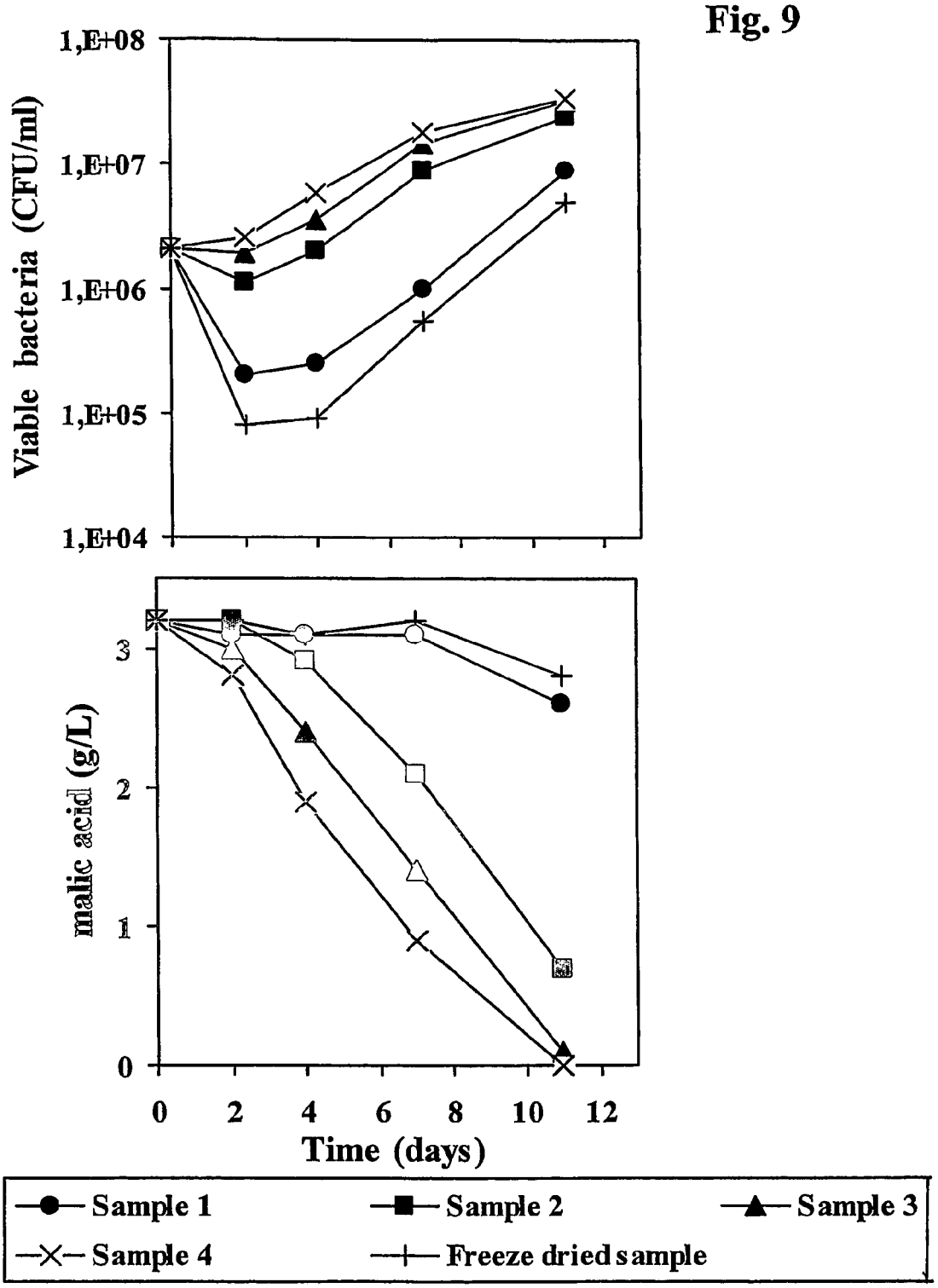

FIG. 9. Number of viable bacteria and malic acid concentration in the experimental wine inoculated with activated samples of the selected non-citric acid fermenting strain *Oenococcus oeni* DSM 15569, and kept at 20° C. The activated samples, named 1, 2, 3, and 4 were harvested from the bacteria activation composition solution described in the text after respectively 8, 16, 24 and 38 hours of activation. Included in the experiment was also the direct inoculation of freeze dried *Oenococcus oeni* DSM 15569.

Figure 10:
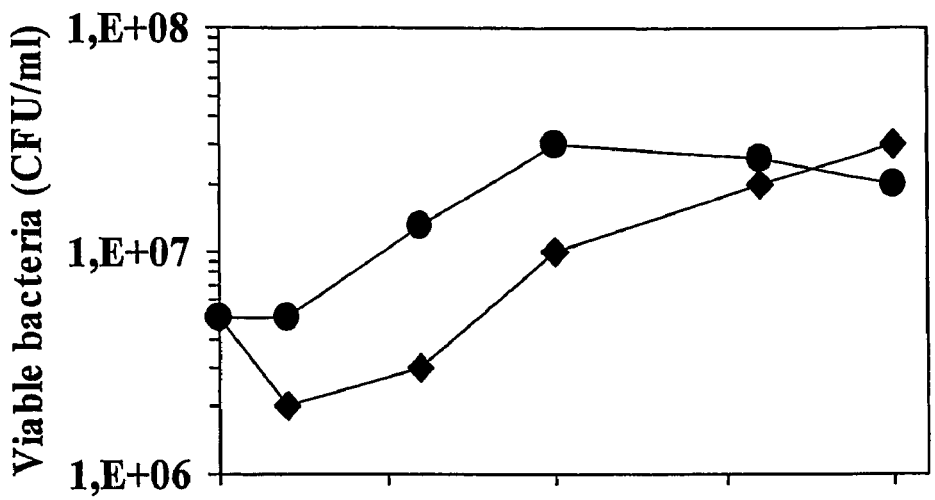
Figure 10:
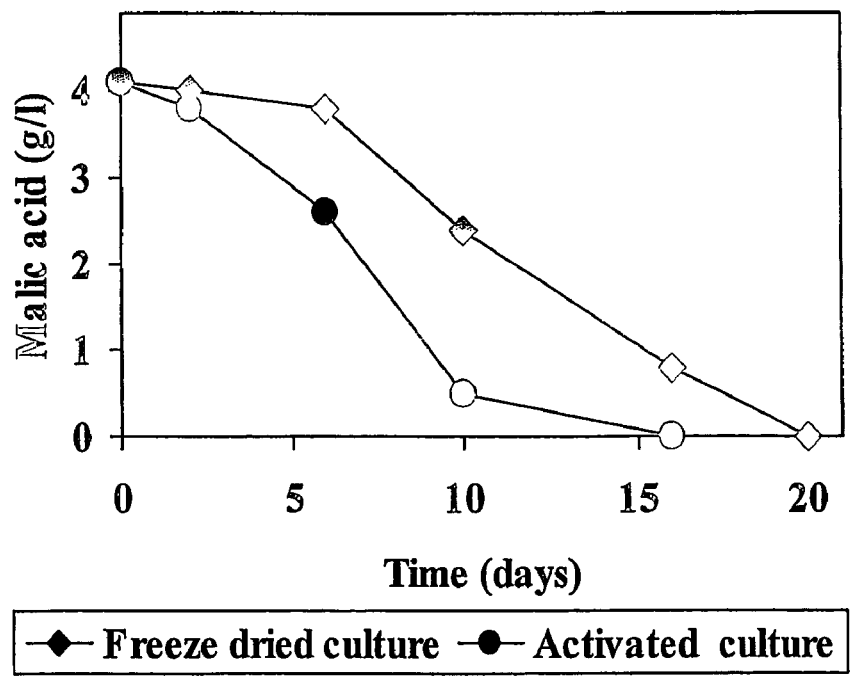

FIG. 10. Number of viable bacteria and malic acid concentration in Chardonnay wine from California inoculated with the commercial product Viniflora oenos from Chr. Hansen A/S, Denmark, which contain *Oenococcus oeni* strain DSM 7008. The freeze dried product was either inoculated directly into the experimental wine as recommended by the producer, or inoculated after 24 hours activation in the activation composition solution described in the text. The wine was kept at 24° C.

FIG. 11. Data for sample A, B, C, and D sampled during the propagation of the selected non-citric acid fermenting mutant strain *Oenococcus oeni* DSM 15571 in the cultivation and adaptation medium shown in FIG. 2.

FIG. 12. Survival rates of the selected non-citric acid fermenting mutant strain *Oenococcus oeni* DSM 15571 in the experimental wine measured 2 days after inoculation of the freeze dried samples A, B, C, and D (FIG. 3). The survival rate was calculated as the % of the inoculated bacteria which was alive day 2 in the wine.

FIG. 13. Data for sample 1, 2, 3, and 4 sampled during the activation of the normal citric acid fermenting strain *Oenococcus oeni* DSM 15568 in the activation composition solution (FIG. 7).

FIG. 14. Survival rates of the normal citric acid fermenting strain *Oenococcus oeni* DSM 15568 in the experimental wine measured 2 days after inoculation of the activated bacteria samples 1, 2, 3, and 4 (FIG. 8). The survival rate was calculated as the % of the inoculated bacteria which was alive day 2 in the wine.

DEFINITIONS

Activation or adaptation of microbial organisms: Both terms refer to methods involving placing a microbial organism under conditions that allow for the physiological changes necessary in order for said microbial organism to survive and grow in a new liquid composition with harsh conditions. In particular, activation or adaptation cover placing a freeze-dried, frozen or otherwise preserved microbial organism in a medium for a specific time period that allow said physiological changes, before said microbial organism is placed in a new liquid composition with harsh conditions. Harsh conditions may for example be low pH, high ethanol content or a mixture of both.

Directly: The term "added directly to" is meant to encompass that the compound, i.e. the frozen or freeze-dried microbial organism is added directly to the liquid composition in the frozen or freeze-dried state without any preceding adaptation, activation and/or expansion.

Ethanol content: the ethanol content is always indicated as volume percent (vol %) unless otherwise specifically indicated, hence an ethanol content of x % refers to x vol % ethanol.

Frozen: The microbial organism is frozen when it is stored at a temperature below 0° C. The microbial organism may be frozen according to any conventional protocol. In general the microbial organism is frozen by mixing said microbial organism with suitable cryoprotectants such as glycerol, gelatine or Na-caseinate and incubating the mixture at a temperature below 18° C.

Freeze dried: Freeze-drying a microbial organism involves freezing said microbial organism generally in the presence of a suitable cryoprotectant, and subsequently removing trapped ice by reducing the pressure and causing it to sublime. The microbial organism according to the present invention may be freeze dried using any conventional method known to the person skilled in the art. For example any of the methods described in "Fundamentals of Freeze Drying, J. D. Mellor, 1978, Academic Press.

DETAILED DESCRIPTION OF THE INVENTION

Microbial Organisms Capable of Fermenting Malic Acid

In one aspect the present invention relates to microbial organisms capable of fermenting malic acid to lactic acid. Preferably, said microbial organism when placed in a medium containing a predetermined amount of citric acid is only capable of degrading at the most 80% of said citric acid. Even more preferably, the microbial organism is only capable of degrading at the most 70%, such as 60%, for example 50%, such as 40%, for example 30%, such as 25%, for example 20%, such as 15%, for example 12%, such as 10% of said citric acid. Hence, it is preferred that the microbial organism is only capable of degrading in the range of 0 to 50%, more preferably 0 to 40%, even more preferably 0 to 30%, yet more preferably 0 to 20% of said citric acid. It is furthermore preferred that the microbial organism is only capable of degrading at the most 50%, more preferably at the most 40%, even more preferably at the most 30%, yet more preferably at the most 20%, even more preferably at the most 10% of said citric acid within for example 3 weeks, more preferably within 2 weeks, such as within 13, for example 12, such as 11, for example 10 days. In a preferred embodiment of the invention the microbial organism is only capable of degrading at the most 50%, more preferably at the most 40%, even more preferably at the most 30%, yet more preferably at the most 20%, even more preferably at the most 15% of the initial citric acid even during long term incubation, such as storage for 30 days, for example for 40 days, for example for 50 days, such as for 60 days, for example for 80 days, such as for 100 days, preferably for at least 40 days, more preferably for at least 50 days.

Because the citric acid degradation in general is delayed compared to the malic acid degradation (see for example FIG. 6B as well as the background section herein above) it is preferred that the microbial organism, when added to a medium comprising malic acid and citric acid (preferably fermented grape juice), said microbial organism has not degraded more 50%, more preferably not more than 40%, even more preferably not more than 30%, yet more preferably not more than 20%, even more preferably not more than 15% of the initial citric acid even 1, such as 2, for example 3, such as 4, for example 5 days, such as 10 days, for example 15 days, such as 20 days, for example 30 days, such as 40 days subsequent to completion of the malolactic fermentation. Within the meaning of the present invention, the malolactic acid fermentation is defined to be completed when the medium (preferably fermented grape juice) comprises at the most 30 mg/L, preferably at the most 15 mg/L malic acid.

In a very preferred embodiment of the invention the microbial organism is not capable of degrading more than 50%, preferably not more than 40%, more preferably not more than 30%, even more preferably not more than 20% of the initial citric acid, for as long as said microbial organism is metabolically active.

Preferably, the microbial organism when placed in a liquid composition comprising a predetermined amount of malic acid is capable of degrading at least 30%, such as 50%, for example 70%, such as 80%, at least 90%, for example at least 95% of said malic acid. Preferably, the microbial organism is capable of degrading in the range of 70 to 100%, more preferably in the range of 80 to 100%, even more preferably in the range of 90 to 100% of said malic acid.

More preferably, the microbial organism when placed in a liquid composition comprising a predetermined amount of malic acid is capable of fermenting at least 30%, such as 50%, for example 70%, such as 80%, at least 90%, for example at least 95% of said malic acid to lactic acid.

In a very preferred embodiment, the microbial organism when placed in a liquid composition comprising a predetermined amount of malic acid is capable of completing malolactic fermentation, i.e. is capable of fermenting malic acid to an end concentration of malic acid of at the most 30 mg/L, more preferably at the most 15 mg/L.

Said degradation of malic acid preferably is completed within at the most 1 month, preferably within at the most 3 weeks, more preferably within at the most 2 weeks, such as 13, for example 12, such as 11, for example 10, such as 9 days.

The liquid composition comprising said predetermined amount of malic acid and/or citric acid furthermore preferably comprises one or more of the following parameters preferably a pH in the range of 2 to 7, preferably in the range of 3 to 6, more preferably in the range of 3 to 5, even more preferably in the range of 3 to 4, for example in the range of 3.1 to 3.8, such as in the range of 3.2 to 3.6, for example around 3.4; and/or preferably an ethanol content of more than 10%, preferably more than 11%, such as more than 12%, preferably an ethanol content in the range of 10 to 14%, such as in the range of 10.5 to 13.5%, for example in the range of 11 to 13%, such as in the range of 11.5 to 12.5%, for example around 10%, such as around 10.5%, for example around 11%, such as around 11.5%, for example around 12%, such as around 12.5%, for example around 13%, such as around 13.5%, for example around 13.9% and/or preferably in the range of 0.1 to 30 g/L sugar, more preferably in the range of 0.5 to 25 g/L, even more preferably in the range of 1 to 20 g/L, such as in the range of 1 to 15 g/L, for example in the range of 1 to 10, such as in the range of 2 to 9, such as in the range of 3 to 8, such as in the range of 4 to 6, for example around 5 g/L sugar and/or preferably in the range of 1 to 50 g/L, more preferably in the range of 1 to 25 g/L, even more preferably in the range of 1 to 10 g/L, for example in the range of 2 to 8 g/L, such as in the range of 2 to 6 g/L, for example in the range of 3 to 4 g/L, such as around 3.3 g/L of malic acid and/or preferably in the range of 1 to 5000 mg/L, more preferably in the range of 10 to 2500 mg/L, even more preferably in the range of 100 to 1000 mg/L, for example in the range of 200 to 800 mg/L, such as in the range of 300 to 600 mg/L, for example in the range of 400 to 500 mg/L, such as around 450 mg/L of citric acid.

It is preferred that said microorganism is incubated with said fermented fruit juice at a temperature of in the range of 15 to 30° C., such as in the range of 20 to 25° C., for example around 23° C.

Preferably, the microbial organism is capable of degrading malic acid and/or citric acid as indicated herein above when said organism is present at a concentration of CFUs (colony forming units) in the range of $1\times10^3$ to $5\times10^{12}$ per ml, preferably in the range of $1\times10^4$ to $5\times10^{10}$ per ml, more preferably in the range of $1\times10^5$ to $5\times10^8$ per ml, for example in the range of $1\times10^6$ to $5\times10^7$ per ml.

In one preferred embodiment of the present invention the microbial organism is capable of reducing malic acid within 9 days to less than 1 g/L, such as less than 0.5 g/L, for example less than 0.1 g/L, such as less than 30 mg/L, for example less than 15 mg/L, when incubated at a temperature of approximately 23° C., when said microbial organism is added directly in a frozen or freeze dried state to a fermented fruit juice at a concentration of CFUs in the range of $1\times10^6$ to $5\times10^7$, wherein said fermented fruit juice is prepared by yeasting a sterile fruit juice without added sulphite resulting in a fermented fruit juice having an ethanol content of 12.0 vol %, pH 3.4, below 5 g/L residual sugar, 3.3 g/L of malic acid, and 450 mg/L of citric acid.

Furthermore, it is preferred that the microbial organism reduces the citric acid content by less than 50%, such as less than 20%, for example less than 10% within 10 days, preferably within 20 days, more preferably within 40 days, for example within 50 days, such as within 100 dayS, when incubated at a temperature of approximately 23° C., when said microbial organism is added directly in a frozen or freeze dried state to a fermented fruit juice at a concentration of CFUs in the range of $1 \times 10^6$ to $5 \times 10^7$ per ml, wherein said fermented fruit juice is prepared by yeasting a sterile fruit juice without added sulphite resulting in a fermented fruit juice having an ethanol content of 12.0 vol %, pH 3.4, below 5 g/L residual sugar, 3.3 g/L of malic acid, and 450 mg/L of citric acid.

The microbial organism according to the present invention preferably has at least one of the following characteristics, when said microbial organism in a frozen or freeze dried state is added directly into a fermented fruit juice:

i) a survival rate which is at least 1% after two days at 23° C. in a fermented sterile fruit juice with a pH of less than 4 and comprising at least 12 vol % ethanol ii) a survival rate which is at least 70% after two days at 17° C. in a fermented sterile fruit juice with a pH of less than 4 comprising at least 13.9 vol % ethanol Preferably, the survival rate is at least 5%, such as at least 10%, for example at least 15%, such as at least 20%, for example at least 25%, such as at least 30%, for example at least 35%, such as at least 40%, for example at least 45%, such as at least 50%, for example at least 55%, such as at least 60%, for example at least 65%, such as at least 70%, for example at least 75%, such as at least 80% after two days at 23° C. in a fermented sterile fruit juice with a pH of less than 4, preferably in the range of 3 to 4, for example in the range of 3.1 to 3.8, such as in the range of 3.2 to 3.6, for example around 3.4 and comprising at least 12 vol % ethanol, preferably around 12 vol % ethanol.

In one embodiment of the invention the microbial organism has a survival rate which is at least 1%, for example at least 5%, such as at least 10%, for example at least 15%, such as at least 20%, for example at least 25%, such as at least 30%, for example at least 35%, such as at least 40%, for example at least 45%, such as at least 50%, for example at least 55%, such as at least 60%, for example at least 65%, such as at least 70%, for example at least 75%, such as at least 80% after two days at 23° C., when added directly to a wine prepared by yeasting a sterile grape fruit juice without added sulphite, said wine having an ethanol content of 12.0 vol %, pH 3.4, below 5 g/L residual sugar, 3.3 g/L of malic acid, and 450 mg/L of citric acid.

In another embodiment of the present invention the survival rate is preferably at least 70%, more preferably at least 75%, for example at least 80%, such as at least 85%, for example at least 90% after two days at 17° C. in a fermented sterile fruit juice with a pH of less than 4, preferably in the range of 3 to 4, for example in the range of 3.1 to 3.8, such as in the range of 3.2 to 3.6, for example around 3.4, wherein the fermented sterile fruit juice comprises at least 13.9 vol % ethanol, preferably around 13.9 vol % ethanol.

In another embodiment of the invention the microbial organism has a survival rate which is in the range of 70% to 100%, more preferably at least 75%, for example at least 80%, such as at least 85%, for example at least 90% after two days at 18° C., when added directly into a wine prepared with 30 ppm $SO_2$ added before the alcoholic fermentation, said wine having an ethanol content of 13.8 vol %, pH 3.5, 1.3 g/L malic acid, and 340 mg/L of citric acid.

In yet another embodiment of the present invention the microbial organism has a survival rate which is at least 80%, such as at least 85%, for example at least 90% after two days at 17° C., when added directly to a wine prepared without $SO_2$ added, said wine having an ethanol content of 13.9 vol %, pH 3.6, 1.7 g/L malic acid, and 320 mg/L of citric acid.

The microbial organism according to the present invention is preferably resistant to one or more different bacteriophages, more preferably the organism is in general resistant to bacteriophages.

Furthermore it is preferred that the microbial organism retains its characteristics during propagation and concentration, i.e. it is preferred that the microbial organism retains its capability of survival, of degrading malic acid and/or citric acid as described herein above during propagation and concentration. Preferably, the microbial organism retains it characteristics after 10, such as after 20, for example after 30, such as after 40, such as after 50, for example after 60, such as after 70, for example after 80, such as after 90, for example after 100 population doublings. It is preferred that the microbial organism retains it characteristics after concentration as described herein below.

In one preferred embodiment of the present invention the microbial organism is a bacterial strain, more preferably the microbial organism is a bacterial strain belonging to the *Oenococcus* family, even more preferably, the microbial organism is an *Oenococcus oeni* strain. For example the microbial organism may be selected from the group consisting of strains deposited under the accession numbers DMS 15569, DMS 15570, and DSM 15571.

Concentrate of Microbial Organisms

In one aspect the present invention relates to a concentrate of microbial organisms comprising or consisting of any of the above mentioned microbial organisms, wherein said concentrate has a content of colony forming units being in the range of $10^9$ to $10^{12}$ per g.

The concentrate may be prepared by any conventional method, for example the concentrate may be prepared by centrifugation, such as by centrifugation of a liquid composition comprising the microbial organisms according to any protocol known to the person skilled in the art. For example the liquid composition may be centrifuged at in the range of centrifugation 2000 to 10,000 g, such as in the range of 3000 to 9000 m for example in the range of 4000 to 8000, such as in the range of 5000 to 7000, for example around 6000 g for in the range of 1 to 120 minutes, for example for in the range of 5 to 60 minutes, such as for around 20 minutes. It is also comprised within the present invention that the concentrate may be prepared using more advanced centrifugation methods, for example methods involving use of different centrifugational forces or by using centrifuges allowing the liquid composition to be added continuously and the eluate to be harvested continuously, Said liquid composition is in general a cultivation medium.

Prior to preparation of the concentrate the microbial organisms may have been cultivated in any conventional medium known to the person skilled in the art.

However, in one preferred embodiment of the invention, the microbial organism has been cultivated in any of the adaptation media described herein below, said adaptation medium comprising at least 6% sugar. Preferably, said adaptation medium comprises at least 5% glucose and/or 5% fructose or at least 3% glucose and at least 3% fructose. Preferably microbial organism has been incubated in said adaptation medium for at least 1-2 hours, such as at least 24 hours, for example around 48 hours prior to harvest by for example centrifugation.

The harvested microbial organisms may in one embodiment of the invention be mixed with any suitable cryoprotectants, for example glycerol, gelatine, Na-caseinate or sucrose and stored frozen at a temperature in the range of −90° C. to 0° C., for example at around 80° C. or around −20° C. Hence, the concentrate may in one embodiment comprise frozen microbial organisms.

It is also comprised within the present invention that the harvested microbial organisms may be dried by for example air drying, spray drying, freeze drying, drum drying or dried using a tray drier, ring-dryer, fluid-bed dryer or vacuum-band dryer. Drying may be done using any suitable protocol known to the person skilled in the art. Hence, the concentrate may in one embodiment comprise dried microbial organisms, such as freeze-dried microbial organisms.

In one embodiment the harvested microbial organisms are freeze dried. Freeze drying may be done according to any suitable protocol known to the person skilled in the art, for example according to any of the protocols described in "Fundamentals of Freeze Drying", J. D. Mellor, 1978, Academic Press.

Preferential Degradation of Malic Acid Over Citric Acid

In one aspect the present invention relates to methods of preferentially degrading malic acid over citric acid in a liquid composition comprising malic acid and citric acid, said method comprising the steps of
  i) Providing a liquid composition comprising malic acid and citric acid;
  ii) Providing any of the microbial organisms described herein above, wherein said microbial organism has been frozen or freeze dried according to any conventional protocol,
  iii) Adding said freeze dried or frozen microbial organism directly to said liquid composition
  iv) incubating said liquid composition and said microbial organism under conditions which allow degradation of at least 70% of the malic acid,
  v) thereby obtaining a final liquid composition comprising less than 30% of the initial malic acid and at least 20% of the initial citric acid.

The liquid composition may in one preferred embodiment of the invention be fruit juice or fermented fruit juice, preferably grape juice or fermented grape juice, such as wine, for example red wine, white wine, rosé or sparkling wine.

The liquid composition preferably has a pH in the range of 2 to 5, such as 3 to 4, for example around 3.4.

Furthermore, the liquid composition preferably comprises in the range of 5 to 15 vol % ethanol, such as 10 to 14 vol % ethanol, for example 11 to 14 vol %, such as 12 to 14 vol %, for example at least 12 vol % ethanol.

It is also preferred that the liquid composition comprises in the range of 0.1 to 30 g/L sugar, more preferably in the range of 0.5 to 25 g/L, even more preferably in the range of 1 to 20 g/L, such as in the range of 1 to 15 g/L, for example in the range of 1 to 10, such as in the range of 2 to 9, such as in the range of 3 to 8, such as in the range of 4 to 6, for example around 5 g/L sugar. More preferably, the liquid composition comprises less than 10 g/L, such as less than 7 g/L, for example less than 5 g/L sugar.

It is furthermore preferred that the liquid composition comprises in the range of 1 to 50 g/L, preferably 1 to 25 g/L, even more preferably in the range of 1 to 10 g/L, for example in the range of 2 to 8 g/L, such as in the range of 2 to 5 g/L, for example in the range of 3 to 4 g/L, such as around 3.3 g/L malic acid.

It is also preferred that the liquid composition comprises in the range of 1 to 5000 mg/L, more preferably in the range of 10 to 2500 mg/L, even more preferably in the range of 100 to 1000 mg/L, for example in the range of 200 to 800 mg/L, such as in the range of 300 to 600 mg/L, for example in the range of 400 to 500 mg/L, such as around 450 mg/L of citric acid. Preferably, the liquid composition comprises in the range of 50 to 2000 mg/L, such as 100 to 1000 mg/L, for example 200 to 800 mg/L, such as 400 to 500 mg/L citric acid.

It is preferred that the final liquid composition comprises at least 50%, preferably at least 60%, more preferably at least 70%, for example at least 75%, such as at least 80% of the initial citric acid.

It is furthermore preferred that the finial liquid composition comprises less than 20%, preferably less than 15%, such as less than 10%, for example less than 5% of the initial malic acid.

The microbial organism is preferably added at a concentration of CFUs in the range of $1 \times 10^3$ to $5 \times 10^{12}$ per ml, preferably in the range of $1 \times 10^4$ to $5 \times 10^{10}$ per ml, more preferably in the range of $1 \times 10^5$ to $5 \times 10^8$ per ml, for example in the range of $1 \times 10^6$ to $5 \times 10^7$ per ml. More preferably, the microbial organism is added at a concentration less than $5 \times 10^7$ CFU per ml of the liquid composition, such as at a concentration of in the range of $1 \times 10^6$ to $5 \times 1$ CFUs per ml of the liquid composition.

The conditions comprises incubation at a temperature in the range of 5 to 40° C., for example 15 to 30° C., such as in the range of 17 to 23° C.

In a preferred embodiment, the method comprises incubation of said liquid composition for at least the time required to obtain the desired fermentation of malic acid, however it is preferred that the incubation is longer, for example at least 5 days, such as at least 10 days, for example at least 15 days, such as at least 20 days, for example at least 30 days, such as at least 40 days more than the time required to obtain the desired malic acid concentration.

In a very preferred embodiment, the method comprises incubation of said liquid composition for a longer period of time than required for completion of malolactic fermentation, for example for at least 5 days, such as at least 10 days, for example at least 15 days, such as at least 20 days, for example at least 30 days, such as at least 40 days more than required for completion of malolactic fermentation.

Induction of Malolactic Fermentation

The present invention also relates to methods of inducing malolactic fermentation, comprising the steps of
  i) Providing a liquid composition comprising malic acid
  ii) Providing a microbial organism, which may be any of the microbial organisms described herein above,
  iii) Incubating said liquid composition with said microbial organism under conditions which allow degradation of malic acid,
  iv) thereby inducing malolactic fermentation The liquid composition is in one preferred embodiment a fruit juice, such as a fermented fruit juice. For example, the liquid composition may be a grape fruit juice, a fermented grape fruit juice or a wine. The wine may for example be selected from the group consisting of red wines, white wines and sparkling wines.

Preferably, the microbial organism is in a frozen or freeze-dried state. The methods thus preferably comprises that the microbial organism in a frozen or freeze-dried state is added directly to the liquid composition, for example to the grape juice or a fermented grape juice.

The microbial organism is preferably added to the liquid composition at a concentration of CFUs in the range of $1\times10^3$ to $5\times10^{12}$ per ml, preferably in the range of $1\times10^4$ to $5\times10^{10}$ per ml, more preferably in the range of $1\times10^5$ to $5\times10^8$ per ml, for example in the range of $1\times10^6$ to $5\times10^7$ per ml. More preferably, the microbial organism is added at a concentration less than $5\times10^7$ CFU per ml of the liquid composition, such as at a concentration of in the range of $1\times10^6$ to $5\times10^7$ CFUs per ml of the liquid composition.

The liquid composition, for example the grape juice or a fermented grape juice preferably has a pH in the range of 2 to 5, such as 3 to 4, for example around 3.4.

Furthermore, the liquid composition such as the grape juice or a fermented grape juice preferably comprises in the range of 5 to 15 vol % ethanol, such as 10 to 14 vol % ethanol, for example 11 to 14 vol %, such as 12 to 14 vol %, for example at least 12 vol % ethanol.

It is also preferred that the liquid composition, such as the grape juice or a fermented grape juice comprises in the range of 0.1 to 30 g/L sugar, more preferably in the range of 0.5 to 25 g/L, even more preferably in the range of 1 to 20 g/L, such as in the range of 1 to 15 g/L, for example in the range of 1 to 10, such as in the range of 2 to 9, such as in the range of 3 to 8, such as in the range of 4 to 6, for example around 5 g/L sugar. More preferably, the liquid composition comprises less than 10 g/L, such as less than 7 g/L, for example less than 5 g/L sugar.

It is furthermore preferred that the liquid composition such as the grape juice or a fermented grape juice comprises in the range of 1 to 50 g/L, preferably 1 to 25 g/L, even more preferably in the range of 1 to 10 g/L, for example in the range of 2 to 8 g/L, such as in the range of 2 to 5 g/L, for example in the range of 3 to 4 g/L, such as around 3.3 g/L malic acid.

It is also preferred that the liquid composition such as the grape juice or fermented grape juice comprises in the range of 1 to 5000 mg/L, more preferably in the range of 10 to 2500 mg/L, even more preferably in the range of 100 to 1000 mg/L, for example in the range of 200 to 800 mg/L, such as in the range of 300 to 600 mg/L, for example in the range of 400 to 500 mg/L, such as around 450 mg/L of citric acid. Preferably, the liquid composition comprises in the range of 50 to 2000 mg/L, such as 100 to 1000 mg/L, for example 200 to 800 mg/L, such as 400 to 500 mg/L citric acid.

In one embodiment of the invention the Malolactic fermentation may for example be induced according to the protocols described in example 3 or 4.

Method of Producing a Microbial Organism

The present invention also describes methods of producing the microbial organism described herein above. The methods comprise the steps of i) Providing a starting microbial organism resistant to a pH below 5 and an ethanol concentration of at least 8%, ii) Subjecting said microbial organism to mutagenesis, thereby obtaining more than one different mutated microbial organism iii) Selecting mutated microbial organisms capable of fermenting malic acid to lactic acid, wherein said microbial organism when placed in a medium containing a predetermined amount of citric acid is only capable of degrading at the most 80% of said citric acid, and wherein the microbial organism has at least one of the following characteristics, when said microbial organism in a frozen or freeze dried state is added directly info a fermented fruit juice:

a) a survival rate which is at least 1% after two days at 23° C. in a fermented sterile fruit juice comprising at least 12 vol % ethanol;

b) a survival rate which is at least 70% after two days at 17° C. in a fermented sterile fruit juice comprising at least 13.9 vol % ethanol The starting microbial organism is preferably capable of fermenting malic acid, more preferably, the starting microbial organism is capable of fermenting malic acid to lactic acid.

The starting microbial organism is preferably resistant to low pH, i.e. to pH below 5, preferably said organism is resistant to pH around 4.5 or lower, more preferably around 4.0 or lower, for example around 3.6 or lower, such as 3.4 or lower, for example said microbial organism is resistant to pH 3.2.

The starting microbial organism is furthermore preferably resistant to high ethanol concentration, i.e. to an ethanol concentration of at least 8 vol %, preferably said organism is resistant to an ethanol concentration of around 9 vol % or higher, more preferably around 10 vol % or higher, for ensample around 11 vol % or higher, such as 12.5 vol % or higher, for example said microbial organism is resistant to an ethanol concentration of around 13%.

In one preferred embodiment of the present invention the starting microbial organism is a bacterial strain, more preferably the starting microbial organism is a bacterial strain belonging to the *Oenococcus* family, even more preferably, the starting microbial organism is an *Oenococcus oeni* strain.

The starting microbial organism may be obtained from any suitable source, it may for example be purchased commercially or isolated from any suitable source known to the skilled person. In one embodiment the starting microbial organism is isolated from a fermented fruit juice, for example from a wine, preferably from a wine with completed spontaneous malolactic fermentation.

Mutagenesis may be done by any conventional method known to the person skilled in the art. In one embodiment mutagenisis comprises incubating the microbial organism in the presence of a mutagenising agent. Said mutagenising agent may for example be selected from the group consisting of ethylmethanesulfunate, N-ethyl-N'-nitro-N-nitrosoguanidine and 1-(2-hydroxyethyl)-1-nitrosourea.

Incubation with the mutagenising agent may be done for any suitable time, for example for in the range of 5 min. to 24 hours, such as in the range of 10 minutes to 12 hours, for example in the range of 15 minutes to 6 hours, such as in the range of 30 minutes to 4 hours, for example in the range of 1 hour to 3 hours, such as in the range of 1.5 hours to 2.5 hours, for example around 2 hours After mutagenisis, mutated microbial organisms with the desired characteristic may be selected, for example mutated microbial organisms with any of the characteristics outlined herein above may be selected.

In one embodiment of the invention microbial organisms with reduced citric acid degradation activity are selected. The selection may for example be performed based on the methods described by G. M. Kempler and L. L. McKay (Appl. Environ. Microbiol.; 1980, 39, 926-927) as described in example 1 herein below.

One non-limiting example of how to prepare a microbial organism according to the present invention is described in example 1.

Preparing Freeze-Dried Microbial Organisms

Surprisingly, the present invention discloses that freeze dried microbial organisms have an increased survival rate after direct inoculation into wine, if the microbial organisms have been cultivated in the adaptation medium described herein below.

Hence, the present invention also relates to methods of preparing a dried microbial organism capable of fermenting malic acid to lactic acid, which has reduced citric acid degrading activity and which is capable of survival after direct inoculation into fermented fruit juice, said method comprising the steps of i) Providing a microbial organism as described herein above ii) Providing an adaptation medium as described herein below comprising at least 6% sugar iii) Incubating said microbial organism in said adaptation medium under conditions allowing growth of said microbial organism iv) Harvesting said microbial organism v) Drying said microbial organism Preferably microbial organism is incubated in said adaptation medium for at least 1.2 hours, such as at least 24 hours, for example around 48 hours prior to harvest. The incubation is preferably at a temperature in the range of 15 to 40° C., such as in the range of 20° C. to 37° C., for example in the range of 25° C. to 35° C., preferably around 30° C. Furthermore, during incubation the pH is preferably kept constant in the range of pH 3.5 to 6.0, such as in the range of pH 4 to 5, preferable around pH 4.5.

The microbial organism may be harvested by any conventional technique known to the person skilled in the art. In general, harvesting said microbial organism comprises centrifugation.

Drying said microbial organism may be done by a number of different methods including, but not limited to air drying, spray drying, freeze drying, drum drying or drying using a tray drier, ring-dryer, fluid-bed dryer or vacuum-band dryer.

Preferably however, the microbial organism is freeze-dried. Freeze-drying may be done according to any protocol known to the skilled person as for example as described in Fundamentals of Freeze Drying, J. D. Mellor, 1978, Academic Press. In general the microbial organism is mixed with a suitable cryoprotective, for example gelatine and/or sucrose and freeze dried using any suitable freeze drier.

Adaptation Medium

The adaptation medium according to the present invention comprises at least 6%, preferably at least 7%, more preferably at least 8%, such as at least 9%, for example at least 10%, such as at least 11% sugar by weight. The sugar may be any suitable sugar for example the sugar may be selected from the group consisting of glucose, fructose, sucrose and maltose. Preferably the sugar is glucose and/or fructose.

In one preferred embodiment the adaptation medium comprises at least 3%, preferably at least 4%, more preferably at least 5%, such as at least 6%, for example at least 7%, such as at least 8%, for example at least 9%, such as at least 10%, for example in the range of 3 to 10%, such as in the range of 4 to 8%, for example in the range of 5 to 6% glucose.

It is also comprised within the present invention that the adaptation medium comprises at least 3%, preferably at least 4%, more preferably at least 5%, such as at least 6%, for example at least 7%, such as at least 8%, for example at least 9%, such as at least 10%, for example in the range of 3 to a 0%, such as in the range of 4 to 8%, for example in the range of 5 to 6% fructose.

In a preferred embodiment the adaptation medium comprises at least 3%, preferably at least 4%, more preferably at least 5%, such as at least 6%, for example at least 7% glucose and at least 3%, preferably at least 4%, more preferably at least 5%, such as at least 6%, for example at least 7% fructose.

The adaptation medium furthermore preferably comprises one or more selected from the group consisting of nitrogen sources, salts, detergents and buffers.

The nitrogen source may be any suitable nitrogen source known to the skilled person. Preferably the nitrogen source comprises amino acids, for example free amino acids or amino acids comprised within a polypeptide or a peptide, It is preferred that the nitrogen source comprises free amino acids and/or short peptides. Short peptides may be prepared by hydrolysing a protein source. In one embodiment of the invention the nitrogen source is selected from the group consisting of yeast extracts, Casein hydrolysate (hydrolysed milk protein) and Bacto peptone (hydrolysed meat).

The salt may for example be $MnSO_4$ or $MgSO_4$, NaCl, $MgCl_2$ or any other suitable salt.

The pH of the adaptation medium is preferably in the range of 2 to 8, more preferably in the range of 3 to 7, even more preferably in the range of 3.5 to 6, even more preferably in the range of 4 to 5, for example around 4.5. The buffer is therefore preferably a buffer capable of buffering the medium to said pH.

The detergent may be any suitable detergent, preferably a detergent containing derivates of unsaturated fatty acids, for example, TWEEN™ 80 polyoxyethylene (2) sorbitan monooleate (CAS Registry No. 9005-65-6) detergent.

In one embodiment of the invention, the adaptation medium is the adaptation medium described in example 2 herein below.

Activation Solution/Composition

In one aspect the present invention relates to an activation composition and an activation solution, wherein said activation solution may be prepared from the activation composition by addition of water. The activation solution is useful for fast and safe activation of microbial organisms prior to inoculation of said microbial organisms into a liquid solution. In particular, freeze dried bacteria can frequently not survive to be inoculated directly into a liquid composition with harsh conditions, such as low pH and/or high ethanol content. Thus prior to inoculation, the microbial organisms must be adapted to survival and growth in said liquid composition. The conventional adaptation procedures are complex and time and labour consuming. They involve one or several steps of propagation and growth in a suitable medium for several days. However, the conventional media are also suitable for the growth of many other microbial organisms. There is therefore a high risk for contamination with spoilage bacteria and yeast as the propagation and adaptation steps under the practical conditions in the wineries can not be conducted under sterile conditions. The risk is especially high because the growth of useful microbial organisms, such as microbial organisms capable of fermenting malic acid to lactic acid, for example *Oenococcus oeni* is much slower compared to the growth of other microbial organisms. The number of bacteria in the activation solution according to the present invention, is very high from the beginning and there is only limited growth or preferably almost no growth or increase in the bacteria population during the activation time. The initial high bacteria number results in a fast drop in the pH and a fast production of large amount of lactic acid from the very high sugar content in the activation solution. Low pH and lactic acid at high concentrations are toxic to most other microbial organisms and thereby greatly reduce the risk for growth of contaminants in the activation solution according to the present invention. The short time of activation also contributes to strongly reduce the risk of contamination. The present inventor has interestingly discovered that a, large drop in pH and a large increase in the lactic acid concentration are factors, which aids adaptation of bacteria to survive direct inoculation into a liquid composition with harsh conditions, for example wine and to initiate the growth in the liquid immediately. In the activation solution according to the present invention, where all the bacteria are present from the beginning, the bacteria adapt to the wine conditions much faster and more effectively than with the conventional adaptation procedures because of the fast drop in pH and fast production of high concentration of lactic acid from the initial high sugar concentration.

Hence, the invention in one aspect relates to an activation solution comprising
  i) A nitrogen source
  ii) In the range of 60 to 140 g sugar per L
  iii) In the range of $5 \times 10^8$ and $5 \times 10^{10}$ colony forming units per ml of a microbial organism capable of fermenting at least one fermentable compound In particular, said activation solution may be useful as an activator of starter cultures, for example malolactic starter cultures. The term starter culture is meant to encompass a composition comprising a microbial organism capable of fermenting a fermentable compound. The activation solution according to the present invention, comprises a very high concentration of sugar, which previously has been thought to inhibit growth of microbial organisms.

The invention also relates to a dry activation composition, wherein in the range of 80 to 200 g of said dry activation composition comprises
  iv) a nitrogen source
  v) In the range of 60 to 140 g sugar
  vi) In the range of $5 \times 10^{11}$ and $5 \times 10^{13}$ colony forming units of a microbial organism capable of fermenting a fermentable compound,
  wherein addition of 1 L water to said dry activation compositions results in said activation solution.

The fermentable compound may be any compound desirable to ferment. In one preferred embodiment of the present invention, the fermentable compound is malic acid. It is thus preferred that the microbial organism is capable of fermenting malic acid, in particular it is preferred that the microbial organism is capable of fermenting malic acid to lactic acid.

The microbial organism is capable of fermenting malic acid to lactic acid, when said microbial organism when placed in a liquid composition comprising a predetermined amount of malic acid it is capable of fermenting at least 30%, preferably at least 50%, more preferably at least 70%, such as at least 80%, at least at least 90%, for example at least at least 95% of said malic acid to lactic acid.

Said degradation of malic acid preferably is completed within at the most 1 month, preferably within at the most 3 weeks, more preferably within at the most 2 weeks, such as 13, for example 12, such as 11, for example 10, such as 9 days.

In one embodiment of the present invention the microbial organism has reduced citric acid degradation activity. For example, said microbial organism, when placed in a medium containing a predetermined amount of citric acid is only capable of degrading at the most 80% of said citric acid. Even more preferably, the microbial organism is only capable of degrading at the most 70%, such as 60%, for example 50%, such as 40%, for example 30%, such as 25%, for example 20%, such as 15%, for example 12%, such as 10% of said citric acid. Hence, it is preferred that the microbial organism is only capable of degrading in the range of 0 to 50%, more preferably 0 to 40%, even more preferably 0 to 30%, yet more preferably 0 to 20% of said citric acid. It is furthermore preferred that the microbial organism is only capable of degrading at the most 50%, more preferably at the most 40%, even more preferably at the most 30%, yet more preferably at the most 20%, even more preferably at the most 10% of said citric acid within for example 3 weeks, more preferably within 2 weeks, such as within 13, for example 12, such as 11, for example 10 days.

The liquid composition comprising said predetermined amount of malic acid and/or citric acid furthermore preferably comprises one or more of the following parameters
  preferably a pH in the range of 2 to 7, preferably in the range of 3 to 6, more preferably in the range of 3 to 5, even more preferably in the range of 3 to 4, for example in the range of 3.1 to 3.8, such as in the range of 3.2 to 3.6, for example around 3.4; and/or
  preferably an ethanol content of more than 10%, preferably more than 11%, such as more than 12%, preferably an ethanol content in the range of 10 to 14%, such as in the range of 10.5 to 13.5%, for example in the range of 11 to 13%, such as in the range of 11.5 to 12.5%, for example around 10%, such as around 10.5%, for example around 11%, such as around 11.5%, for example around 12%, such as around 12.5%, for example around 13%, such as around 13.5%, for example around 13.9% and/or
  preferably in the range of 0.1 to 30 g/L sugar, more preferably in the range of 0.5 to 25 g/L, even more preferably in the range of 1 to 20 g/L, such as in the range of 1 to 15 g/L, for example in the range of 1 to 10, such as in the range of 2 to 9, such as in the range of 3 to 8, such as in the range of 4 to 6, for example around 5 g/L sugar and/or
  preferably in the range of 1 to 50 g/L, more preferably in the range of 1 to 25 g/L, even more preferably in the range of 1 to 10 g/L, for example in the range of 2 to 8 g/L, such as in the range of 2 to 6 g/L, for example in the range of 3 to 4 g/L, such as around 3.3 g/L of malic acid and/or preferably in the range of 1 to 5000 mg/L, more preferably in the range of 10 to 2500 mg/L, even more preferably in the range of 100 to 1000 mg/L, for example in the range of 200 to 800 mg/L, such as in the range of 300 to 600 mg/L, for example in the range of 400 to 500 mg/L, such as around 450 mg/L of citric acid.

It is preferred that said microorganism is incubated with said liquid composition at a temperature of in the range of 15 to 30° C., such as in the range of 20 to 25° C., for example around 23° C.

Preferably, the microbial organism is capable of degrading malic acid and/or citric acid as indicated herein above when said organism is present in a concentration in the range of $1 \times 10^3$ to $5 \times 10^{12}$ per ml, preferably in the range of $1 \times 10^4$ to $5 \times 10^{10}$ per ml, more preferably in the range of $1 \times 10^5$ to $5 \times 10^8$ per ml, for example in the range of $1 \times 10^6$ to $5 \times 10^7$ per ml.

In one preferred embodiment of the present invention the microbial organism is capable of reducing malic acid within 9 days to less than 1 g/L, such as less than 0.5 g/L, for example less than 0.1 g/L, when incubated at a temperature of approximately 23° C., when said microbial organism is added directly in a frozen or freeze dried state to a fermented fruit juice at a concentration of CFUs in the range of $1 \times 10^6$ to $5 \times 10^7$ per ml, wherein said fermented fruit juice is prepared by yeasting a sterile fruit juice without added sulphite resulting in a fermented fruit juice having an ethanol content of 12.0 vol %, pH 3.4, below 5 g/L residual sugar, 3.3 g/L of malic acid, and 450 mg/L of citric acid.

In another embodiment, it is preferred that the microbial organism reduces the citric acid content by less than 50%, such as less than 20%, for example less than 10% within 10 days, when incubated at a temperature of approximately 23° C., when said microbial organism is added directly in a frozen or freeze dried state to a fermented fruit juice at a concentration of CFUs in the range of $1\times10^6$ to $5\times10^7$ per ml, wherein said fermented fruit juice is prepared by yeasting a sterile fruit juice without added sulphite resulting in a fermented fruit juice having an ethanol content of 12.0 vol %, pH 3.4, below 5 g/L residual sugar, 3.3 g/L of malic acid, and 450 mg/L of citric acid.

In one preferred embodiment of the present invention, the freeze-dried or frozen microbial organism have a low surviving rate or is not capable of surviving at all when directly inoculated into a fermented fruit juice, i.e. the microbial organism does not have one or more of the characteristics mentioned herein below. In a preferred embodiment the microbial organism does not have any of the characteristics mentioned herein below. It is however comprised within the invention that the freeze-dried or frozen microbial organism may have a high survival rate when directly inoculation into a fermented fruit juice. Such microbial organisms may however in general survive better and start growth faster when inoculated into fermented fruit juice if they have been pre-incubated in the activation solution according to the invention.

Hence, the microbial organism may or may not have one or more of the following characteristics, when said microbial organism in a frozen or freeze dried state is added directly into a fermented fruit juice:

i) a survival rate which is at least 10% after two days at 23° C. in a fermented sterile fruit juice with a pH of less than 4 and comprising at least 12 vol % ethanol ii) a survival rate which is at least 70% after two days at 17° C. in a fermented sterile fruit juice with a pH of less than 4 comprising at least 13.9 vol % ethanol For example, the survival rate may be at least 15%, such as at least 20%, for example at least 25%, such as at least 30%, for example at least 35%, such as at least 40%, for example at least 45%, such as at least 50%, for example at least 55%, such as at least 60%, for example at least 65%, such as at least 70%, for example at least 75%, such as at least 80% after two days at 23° C. in a fermented sterile fruit juice with a pH of less than 4, preferably in the range of 3 to 4, for example in the range of 3.1 to 3.8, such as in the range of 3.2 to 3.6, for example around 3.4 and comprising at least 12 vol % ethanol, preferably around 12 vol % ethanol.

Preferably, the microbial organism after activation for more than 4 hours, preferably for more than 5 hours, for example for in the range of 5 hours to 2 weeks, such as in the range of 6 hours to 1 week, for example for in the range of 6 hours to 5 days, such as in the range of 7 hours to 3 days, for example for in the range of 7 hours to 2 days, such as in the range of 8 hours to 48 hours, for example for in the range of 8 hours to 46 hours, such as around 4 hours, for example around 8 hours, such as around 19 hours, for example around 46 hours in the activation solution has a survival rate which is at least 3%, preferably at least 5%, more preferably at least 10%, even more preferably at least 20%, yet more preferably at least 30%, even more preferably at least 33%, yet even more preferably at least 40%, such as at least 50%, for example at least 60%, such as at least 70%, for example at least 80%, such as at least 90%, preferably at least 94%, for example at least 95%, such as around 100% after two days at 23° C. when inoculated into a fermented fruit juice having an ethanol content of at least 12.0 vol %.

More preferably, the microbial organism after activation for more than 4 hours, preferably for more than 5 hours, for example for in the range of 5 hours to 2 weeks, such as in the range of 6 hours to 1 week, for example for in the range of 6 hours to 5 days, such as in the range of 7 hours to 3 days, for example for in the range of 7 hours to 2 days, such as in the range of 8 hours to 48 hours, for example for in the range of 8 hours to 46 hours, such as around 4 hours, for example around 8 hours, such as around 19 hours, for example around 46 hours in the activation solution has a survival rate which is at least 3%, preferably at least 5%, more preferably at least 10%, even more preferably at least 20%, yet more preferably at least 30%, even more preferably at least 33%, yet even more preferably at least 40%, such as at least 50%, for example at least 60%, such as at least 70%, for example at least 80%, such as at least 90%, preferably at least 94%, for example at least 95%, such as around 100% after two days at 23° C. when inoculated into a fermented fruit juice prepared by yeasting a sterile grape fruit juice without added sulphite, said fermented fruit juice having an ethanol content of 12.0 vol %, pH 3.4, below 5 g/L residual sugar, 3.3 g/L of malic acid, and 450 mg/L of citric acid The microbial organism according to the present invention is preferably resistant to one or more different bacteriophages, more preferably the organism is in general resistant to bacteriophages.

Furthermore it is preferred that the microbial organism retains its characteristics during propagation and concentration, i.e. it is preferred that the microbial organism retains its capability of survival, of degrading malic acid and/or citric acid as described herein above during propagation and concentration. Preferably, the microbial organism retains it characteristics after 10, such as after 20, for example after 30, such as after 40, such as after 50, for example after 60, such as after 70, for example after 80, such as after 90, for example after 100 population doublings. It is preferred that the microbial organism retains it characteristics after concentration as described herein below.

In one preferred embodiment of the present invention the microbial organism is a bacterial strain, preferably the microbial organism is selected from the group consisting of bacteria belonging to the Oenococcus family and the Lactobacillus family.

More preferably, the microbial organism is selected from the group consisting *Oenococcus oeni, Lactobacillus hilgardii, Lactobacillus brevis, Lactobacillus casei* and *Lactobacillus plantarum*. Even more preferably the microbial organism is selected from the group consisting *Oenococcus oen*, and *Lactobacillus plantarum*.

For example, the microbial organism may be selected from the group consisting of the bacterial strains MBR Alpha, MBR Beta, MBR 31, MBR 41 and MBR OSU available from Lallemand Inc., Montreal, Canada. Said strains may survive direct inoculation into wine. The microbial organism may also be selected from the group consisting of Inobacter (IB), OSU, ProVino, MCW, 3X, and MT01 available from Lallemand Inc., Montreal, Canada. Said strains require adaptation prior to inoculation into wine. In one preferred embodiment of the invention the microbial organism is MT01 available from Lallemand Inc., Montreal, Canada, which has reduced citric acid degradation activity. The microbial organism may also be selected from the group consisting of Viniflora oenos and Viniflora CH35 available from Chr. Hansen A/S, Hoersholm, Denmark. These strains may be inoculated directly into wine.

In one embodiment the microbial organism may be any of the microbial organisms described in international patent application WO 93/20180, which is hereby incorporated herein in its entirety.

In one preferred embodiment of the invention, the microbial organism is a bacteria belonging to the *Oenococcus* family, more preferably the microbial organism is an *Oenococcus oeni*. For example, the microbial organism may selected from the group consisting of microbial organisms deposited under the accession numbers DSM 15568, DSM 7008, DMS 15569, DMS 15570, and DSM 15571.

In one embodiment of the present invention the microbial organism is any of the microbial organisms described herein above in the section "Microbial organisms capable of fermenting malic acid".

The sugar in the dry activation composition and in the activation solution according to the present invention may be any suitable sugar. For example the sugar may be selected from the group consisting of glucose, fructose, sucrose and maltose. Preferably the sugar is glucose and/or fructose.

The activation solution according to the present invention comprises in the range of 60 to 140 g sugar per L, preferably in the range of 70 to 130 g sugar per L, more preferably in the range of 80 to 120 g sugar per L, for example in the range of 90 to 110 g sugar per L, such as around 100 g sugar per L.

Accordingly, the activation composition preferably comprises in the range of 60 to 140 g sugar, preferably in the range of 70 to 130 g sugar, more preferably in the range of 80 to 120 g sugar, for example in the range of 90 to 110 g sugar, such as around 100 g sugar per 80 to 200 g of said dry activation composition. For example, in the range of 110 to 150 g of said dry activation composition comprises in the range of 80 to 110 g, such as 90 to 110 g, for example 95 to 105 g sugar The activation solution may for example comprise in the range of 30 g to 100 g, such as in the range of 30 to 90 g, for example in the range of 30 to 80 g, such as in the range of 35 to 70 g, such as 40 to 80 g, for example in the range of 40 to 60 g, such as in the range of 45 to 55 g, for example around 50 g glucose per L.

Thus the dry activation composition may comprise in the range of 30 g to 100 g, such as in the range of 30 to 90 g, for example in the range of 30 to 80 g, such as in the range of 35 to 70 g, such as 40 to 80 g, for example in the range of 40 to 60 g, such as in the range of 45 to 55 g, for example around 50 g glucose per 80 to 200 g of said dry activation composition.

The activation solution may for example comprise in the range of 30 g to 100 g, such as in the range of 30 to 90 g, for example in the range of 30 to 80 g, such as 40 to 80 g, such as in the range of 35 to 70 g, for example in the range of 40 to 60 g, such as in the range of 45 to 55 g, for example around 50 g fructose per L.

Thus the dry activation composition may comprise in the range of 30 g to 100 g, such as in the range of 30 to 90 g, for example in the range of 30 to 80 g, such as 40 to 80 g, such as in the range of 35 to 70 g, for example in the range of 40 to 60 g, such as in the range of 45 to 55 g, for example around 50 g fructose per 80 to 200 g of said dry activation composition.

Preferably, the activation solution or the activation composition comprises both glucose and fructose, for in the range of 30 to 80 g, such as 40 to 80 g, such as in the range of 35 to 70 g, for example in the range of 40 to 60 g, such as in the range of 45 to 55 g, for example around 50 g glucose and in the range of 30 to 80 g, such as 40 to 80 g, such as in the range of 35 to 70 g, for example in the range of 40 to 60 g, such as in the range of 45 to 55 g, for example around 50 g fructose per L or per 80 to 200 g of said dry activation composition.

The activation solution and/or the activation composition furthermore preferably comprises one or more selected from the group consisting of nitrogen sources, salts and chemical compound with buffering capacity (buffer). Preferably the activation solution and/or the activation composition comprises all.

The nitrogen source may be any suitable nitrogen source known to the skilled person. Preferably the nitrogen source comprises amino acids, for example free amino acids and/or amino acids comprised within a polypeptide or a peptide, It is preferred that the nitrogen source comprises free amino acids and/or short peptides. Short peptides are usually prepared by hydrolysing a protein source. In one embodiment of the invention the nitrogen source is selected from the group consisting of yeast extracts, Casein hydrolysate (hydrolysed milk protein), Bacto peptone (hydrolysed meat) and other hydrolysed proteins.

The salt may for example be $MnSO_4$ or $MgSO_4$, NaCl, $MgCl_2$ or any other suitable salt.

The pH of the adaptation medium is preferably in the range of 2 to 8, more preferably in the range of 3 to 7, even more preferably in the range of 4 to 6, for example around 4.9. The chemical compound with buffering capacity is therefore preferably a buffer capable of buffering the medium to said pH. For example the chemical compound may be selected from the group consisting of tartaric acid, malic acid, lactic acid, phosphate and citrate.

In one embodiment of the present invention the dry activation composition is the dry activation composition described in example 5, wherein the freeze dried bacteria (DSM 15568) used in example 5 optionally may be substituted with any of the microbial organisms mentioned above in this section.

Induction of Fermentation

The present invention also relates to methods of inducing fermentation in a liquid composition comprising a fermentable compound comprising the steps of i) Providing either a dry activation composition or an activation solution as described herein above, wherein the microbial organism comprised within said composition/solution is capable of fermenting said fermentable compound ii) If a dry composition is provided, adding water to said dry composition, thereby obtaining an activation solution iii) Incubating said activation solution for an activation time under activation conditions iv) Providing a liquid composition comprising said fermentable compound v) Inoculating said liquid composition with said activation solution vi) Thereby inducing fermentation in said liquid composition The liquid composition may be any suitable liquid composition in which it is desirable to induce a fermentation process, for example the liquid composition may be a fruit juice or a fermented fruit juice, such as a grape fruit juice or fermented grape fruit juice. A fermented grape fruit juice may for example be a wine, such as a red wine, white wine, sparkling wine or rosé wine.

The activation time may be selected according to the specific embodiment. In general a longer activation time results in better survival after inoculation up to an activation time of approximately 2 days. Preferably, the activation time is thus more than 4 hours, preferably for more than 5 hours, for example for in the range of 5 hours to 2 weeks, such as in the range of 6 hours to 1 week, for example for in the range of 6 hours to 5 days, such as in the range of 7 hours to 3 days, for example for in the range of 7 hours to 2 days, such as in the range of 8 hours to 48 hours, for example for in the range of 8 hours to 46 hours, such as around 4 hours, for example around 8 hours, such as around 19 hours, for example around 46 hours.

Preferably, the activation time is selected so that the microbial organism has a survival rate which is at least 3%, preferably at least 5%, more preferably at least 10%, even more preferably at least 20%, yet more preferably at least 30%, even more preferably at least 33%, yet even more preferably at least 40%, such as at least 50%, for example at least 60%, such as at least 70%, for example at least 80%, such as at least 90%, preferably at least 94%, for example at least 95%, such as around 100% after two days at 23° C. when inoculated into a fermented fruit juice having an ethanol content of at least 12.0 vol %.

The activation conditions preferably comprises incubation at a temperature in the range of 10° C. to 40° C., for example 15° C. to 35° C., such as 15° C. to 30° C., for example 18° C. to 25° C., such as 20° C. to 25° C., for example around 23° C.

The fermentable compound may be any compound desirable to ferment. In one preferred embodiment of the present invention, the fermentable compound is malic acid.

Preferably around 1 L of water is added to in the range of 80 to 200 g of the dry activation composition comprising in the range of 60 to 140 g sugar. Water may for example be tap water, distilled water or sterile water.

Deposition of Microbial Organisms

The present invention refers to microbial organisms deposited under the accession numbers DSM 15568, DSM 15569, DSM 15570, and DSM 15571 at DSMZ—Deutsche Sammlung von Mikroorganismen und Zellkulturen GmbH, Mascheroder Weg 1b, 38124 Braunschweig, GERMANY. Details regarding the deposited microbial organisms are given in the table below.

| Accession number | Date of deposit | Taxonomic description |
|---|---|---|
| DSM 15568 | 14 Apr., 2003 | Oenococcus oeni |
| DSM 15569 | 14 Apr., 2003 | Oenococcus oeni |
| DSM 15570 | 14 Apr., 2003 | Oenococcus oeni |
| DSM 15571 | 14 Apr., 2003 | Oenococcus oeni |

The deposits were made under the provisions of the Budapest Treaty on the International recognition of the Deposit of Microorganisms for the Purpose of Patent Procedure and Regulations thereunder.

EXAMPLES

Example 1

Selection of Non-Citric Acid Fermenting Mutants of Oenococcus oeni

Strains of Oenococcus oeni with resistance to pH below 3.2 and more than 13 vol % ethanol were isolated from different wines with completed spontaneously malolactic fermentation using techniques known in the art.

The objective of the mutagenesis of the Oenococcus oeni strains was to obtain mutants where the citric acid metabolism, depicted in FIG. 1, was eliminated. Mutagenesis of the Oenococcus oeni strains was carried out by adding 0.2 ml ethylmethanesulfunate to 10 ml of a stationary phase culture of Oenococcus oeni. After incubation of the mixture for two hours at 30° C., 0.1 ml was transferred to 10 ml fresh cultivation medium and incubated for 48 hours at 30° C. The composition of the cultivation medium was by weight:
2% glucose
2% fructose
2% yeast extract (Oxoid Ltd., England)
0.02% $MnSO_4 \cdot 7H_2O$
0.2% TWEEN™80 detergent
pH adjusted to 5.0 with 20% NaOH.

From the stationary phase culture, spread plates were made using the methods described by G. M. Kempler and L. L. McKay (Appl. Environ. Microbiol.; 1980, 39, 926-927) except that the agar used had the following composition:
1% glucose
1% fructose
1% yeast extract (Oxoid Ltd., England)
0.02% $MnSO_4 \cdot 7H_2O$
0.2% TWEEN™80 detergent
2% Agar (Agar-agar, Merck, Germany)
pH adjusted to 5.5 with 20% HCl The plates were incubated for 10 days at 30° C. On the plates white colonies containing mutated non-citric acid fermenting bacteria could be differentiated from blue colonies containing normal citric acid fermenting bacteria.

Example 2

Preparation of Experimental Wine for Evaluation of Selected Non-Citric Acid Fermenting Oenococcus oeni Mutants A 5 liter sterile glass container was added 4 liter of sterile Biotta grape juice (Biotta AG, Switzerland) adjusted with sucrose to a total sugar concentration of 212 g/l and inoculated with 1.5 g of active dry yeast (Saccharomyces cerevisiae, Saint George S101, Fould-Springer, France). The juice was incubated at 23° C. After 14 days the alcoholic fermentation was completed and the wine was adjusted to pH 3.4 with 20% HCl. The concentration of total glucose and fructose in the wine was below 5 g/liter, the ethanol concentration was 12.0% (v/v), and the L-malic acid and citric acid concentration was 3.3 g/liter and 0.45 g/liter respectively. The glucose, fructose, ethanol, malic acid, and citric acid concentrations were determined by the enzymatic test kits of Boehringer Mannheim, Germany.

Examination of Selected Non-Citric Acid Fermenting Oenococcus oeni Mutants.

For unknown reason the growth of the selected mutants in commercially available cultivation media for lactic acid bacteria (MRS Broth from Oxoid Ltd.) were slow compared to the non-mutated strains. Also when pre-cultivated in MRS Broth for 48 hours at 30° C. and inoculated directly from the cultivation broth into the experimental wine, the survival rate of the inoculated mutants in the wine measured 2 days after inoculation were 20-50 times lower compared to the non-mutated strains. Clearly, the mutation in the selected strains somehow effect the growth and the ability to survive direct inoculation into wine.

Examination of new cultivation and adaptation medium for the production of non-citric acid fermenting Oenococcus oeni mutants.

The selected non-citric acid fermenting Oenococcus oeni strain DSM 15571 were grown in the cultivation and adaptation medium of the following composition by weight:
5.5% glucose
5.5% fructose
3.9% yeast extract (Oxoid Ltd., England)

0.02% MnSO$_4$.7H$_2$O
0.2% TWEEN™80 detergent
pH adjusted to 4.5 with 20% HCl.

The cultivation and adaptation medium was sterilized at 121° C. for 10 minutes and cooled to 30° C.

The medium was inoculated with the non-citric acid fermenting Oenococcus oeni strain DSM 15571 which had been pre-cultured in a medium with the same composition for 48 hours at 30° C.

The inoculated medium was held at 30° C. and at constant pH 4.5 by addition of 20% NaOH. FIG. 2 show the growth of the *Oenococcus oeni* strain measured as the optical density at 600 nm (OD600), the total concentration of sugar (glucose+fructose), and the calculated amount of fermented sugar in the medium.

At different times during the fermentation, 200 ml samples were removed. The name and time of the sampling, the OD600, the total concentration of sugar, and the calculated amount of fermented sugar in the samples are shown in Table 1. The bacteria were harvested from the sample by centrifugation. The bacteria concentrate from the centrifugation was re-suspended in sterile water containing 4% gelatine as cryoprotective and freeze dried using techniques known in the art.

The enumeration of viable bacteria in the freeze dried product and in inoculated wine was performed after appropriate dilution in water containing 0.1% peptone and 0.9% NaCl, followed by pour plate seeding in agar. The composition of the agar used was by weight:

2% glucose
2% fructose
2% yeast extract (Oxoid Ltd., England)
0.02% MnSO$_4$$^+$7H$_2$O
0.2% TWEEN™80 detergent
2% Agar (Agar-agar, Merck, Germany) pH adjusted to 5.0 with 20% HCl.

The agar was autoclaved at 125° C. for 10 minutes and cooled to 45° C. before use. Viable counts were obtained as the number of colony forming units (CFU) after incubation at 30° C. for 7 days Based on the determination of the CFU/g in the freeze dried samples, 4 L experimental wine was inoculated directly with the freeze dried samples of *Oenococcus oeni* DSM 15571 to an initial concentration of 5×10$^6$ CFU/ml wine. The wine was incubated at 23° C. FIG. 3 shows the CFU/ml measured in the wines inoculated with sample A, B, C, and D. Table 2 show the survival rate of *Oenococcus oeni* DSM 15571 in the wine day 2 determined as % of the initial inoculation level.

The results in FIG. 3 shows that there was a minimum in the CFU/ml measured in the wine 2 days after inoculation after which time the bacteria started to grow. FIG. 3 and Table 2 also shows that there was a very large difference in the survival of the inoculated bacteria samples in the wine after 2 days. Sample A, which was harvested from the fermentor when 44.8 g/L of the sugar was fermented (Table 1), survived poorly the inoculation into wine. Only 0.4% of the inoculated bacteria was alive in the wine after 2 days (Table 2). However, for sample B, C, and D, which was harvested from the fermentor when respectively 68, 84, and 100 g/L of the sugar was fermented, the survival rate of the bacteria day 2 in the wine increased to 10.2%, 44%, and 98% respectively. The results shows that there is a clear increase in the adaptation of the non-citric acid fermenting strain *Oenococcus oeni* DSM 15571 to survive direct inoculation into wine when more than 44.8 g/L of the sugar is fermented during the propagation of the bacteria mutant.

Example 3

Induction of Malolactic Fermentation in the Experimental Wine by Direct Inoculation with Freeze Dried Preparation of Non-Citric Acid Fermenting *Oenococcus oeni*

The malolactic fermentation induced by freeze dried preparation of the non-citric acid fermenting strain *Oenococcus oeni* DSM 15571, prepared as described for sample D in Example 2, was examined in 4 L experimental wine inoculated directly with the freeze dried sample to an initial concentration of 2×10$^6$ CFU/ml wine.

The results of this experiment are shown in FIG. 4 from which it appears that the survival rate of the strain was 90% measured 2 days after inoculation after which time the strains started to multiply in the wine and degrade the malic acid, which was exhausted after 10 days. The non-citric acid fermenting mutant did not degrade the citric acid in the wine and the concentration of acetic acid increased only from 390 to 450 mg/L during the experiment.

Example 4

Induction of Malolactic Fermentation in California Wines by Direct Inoculation with Freeze Dried Preparation of Non-Citric Acid Fermenting *Oenococcus oeni* Strains Freeze dried preparation of three non-citric acid fermenting mutants of *Oenococcus oeni*, DSM 15570, DSM 15569, and DSM 15571 were tested by direct inoculation into 250 L oak barrels containing different wines form Russian River and Sonoma, Calif. (see description of the figures for further details) or by direct inoculation into the experimental wine described in example 2. All freeze dried preparations were prepared as previously described for sample D in Example 2. For comparison, a freeze dried commercial culture (Viniflora oenos from Chr. Hansen A/S, Denmark) of *Oenococcus oeni* (strain DSM 7008) with a normal citric acid metabolism was included.

The results from the experiments are shown in FIG. 5 and FIG. 6A. In all of the inoculated barrels the survival rate of the mutants measured two days after inoculation was 65 to 100%. All barrels completed the malic acid degradation within 19 to 24 days. The results show that the non-citric acid fermenting mutant strains did not degrade the citric acid in the wine and the concentration of acetic acid only increased 35 to 70 mg/L during the trials which was significantly less than the 221 to 247 mg/L increase measured for the normal citric acid fermenting strain.

FIG. 6B shows the degradation of malic and citric acid in experimental wine after direct inoculation of freeze dried bacteria of strains DSM; 15569 and 15570. All freeze dried preparations were prepared as previously described for sample D in Example 2. The experimental wine was prepared as described in example 2 except that it contained 3.4 g/liter of malic acid and 0.49 g/liter of citric acid. For comparison Viniflora oenos and Viniflora CH35 (both available from Chr. Hansen A/S) were included. The experiment was conducted at 23° C. As is apparent malic acid fermentation is completed after 8 to 13 days. In the test strains essentially no citric acid is degraded, whereas in the control experiments, citric acid degradation is completed after 13 and 20 days respectively. After 50 days of incubation the wine incubated with DSM 15569 comprised 470 mg/L citric acid and the wine incubated with DSM 15570 comprised 440 mg/L citric acid. The starting concentration of citric acid in the wine was 490 mg/L.

Example 5

Blending of New Dry Activation Composition

A dry activation composition was produced by blending the following components:
50 g glucose
50 g fructose
10 g yeast extract (Oxoid Ltd., England)
0.45 g tartaric acid
0.1 g $MnSO_4 \cdot 7H_2O$
20 g freeze dried *Oenococcus oeni* strain DSM 15568 (normal citric acid fermenting strain)

Tartaric acid is an organic acid with buffer capacity. The amount of tartaric acid in the above composition was chosen so that the dry composition, when water was added to a total of 1 L, resulted in a pH of 4.9 in the solution. The freeze dried *Oenococcus oeni* strain DSM 15568 in the composition contained $4 \times 10^{11}$ CFU/g and was prepared as described for sample A in Example 2.

Examination of New Dry Activation Composition.

The blended dry activation composition was re-hydrated by addition of water to a total of 1 L followed by incubation of the activation composition solution at 23° C. The activation composition solution, which from start contained a total of 100 g sugar/L and $8 \times 10^9$ CFU/ml of *Oenococcus oeni* strain DSM 15568 was followed by the determination of total sugar/L, pH and CFU/ml. The results are shown in FIG. 7 from which it appear that during the 46 hours of activation the number of viable bacteria measured as CFU/ml was almost constant in the activation solution. The total sugar concentration decreased within 4 hours to less than 55 g/L and ended at 15 g/L after 46 hours of activation while the pH decreased fast from the initial pH of 4.9 to pH 4.0 after 4 hours and ended at pH 3.43 after 46 hours.

At different time during the activation four samples, named 1, 2, 3, and 4 were removed from the solution. The name and time of the sampling, the pH, the amount of total sugar, and the calculated amount of sugar fermented in the samples are shown in Table 3.

1 ml of the samples 1, 2, 3, and 4 were inoculated directly into 2.5 L experimental wine in a 5 L container which resulted in an initial bacteria number of $3.2 \times 10^6$ CFU/ml. The number of viable bacteria and the malic acid concentration in the wine was followed and the results are shown in FIG. 8. Table 4 show the % survival of the inoculated bacteria measured day 2 in the wine. Included in the experiment was also the direct inoculation into the experimental wine of freeze dried *Oenococcus oeni* strain DSM 15568 prepared as described for sample A in Example 2. The freeze dried preparation was inoculated to a concentration of $3.2 \times 10^6$ CFU/ml.

FIG. 8 shows that there was a minimum in the CFU/ml measured in the wine 2 days after inoculation after which time the bacteria started to grow. The results in FIG. 8 and Table 4 shows clearly that the bacteria inoculated from the activation solution survived better in the wine and conducted a faster malolactic fermentation than the freeze dried bacteria inoculated directly into the wine. The results further shows that the survival rate and the malic acid degradation performance of the bacteria in the wine increased with the incubation time of the bacteria in the activation solution. The survival rate day 2 in the wine of bacteria from samples taken from the activation solution after 4, 8, 19, and 46 hours incubation was 3%, 33%, 94%, and 100% respectively and the increase in the survival rates resulted in a significantly increased speed of the malolactic fermentation.

Example 6

Examination of New Dry Activation Composition Containing Non-Citric Acid Fermenting *Oenococcus oeni* Strain A dry activation composition was produced as described in Example 5 except for the bacteria strain where 15 g freeze dried product of the selected non-citric acid fermenting mutant strain *Oenococcus oeni* DSM 15569 was used and that the amount of sugar was changed to 55 g glucose and 55 g fructose. The freeze dried strain was prepared as described for sample A in Example 2 and the product contained $3.5 \times 10^{11}$ CFU/g.

The dry activation composition was re-hydrated by addition of water to a total of 1 L which resulted in a bacteria concentration of $5.3 \times 10^9$ CFU/ml. The activation solution was incubated at 23° C. After 8, 16, 24 and 38 hours incubation respectively, a sample of 1 ml of the activated bacteria solution was inoculated directly into 2.5 L experimental wine in a 5 L container resulting in an initial bacteria number of $2.1 \times 10^6$ CFU/ml. The samples was named 1, 2, 3, and 4 respectively. Also included in the examination was the direct inoculation of the wine with freeze dried *Oenococcus oeni* strain DSM 15569 to a concentration of $2.1 \times 10^6$ CFU/mL. The freeze dried strain was prepared as described for sample A in Example 2. The wine was kept at 20° C. and followed by the determination of CFU/ml and malic acid concentration.

FIG. 9 show the results from the 5 wines. The survival rates measured day 2 in the wines inoculated directly with freeze dried bacteria and sample 1, 2, 3, and 4 from the activated bacteria solution were 4%, 10%, 52%, 90% and 100% respectively. Clearly, the activated bacteria survived much better in the wine than the direct inoculated freeze dried bacteria and the survival rate in the wine for the activated bacteria increased with the incubation time in the activation solution. The malolactic activity in the wines clearly reflected the different survival rates. The wines with the highest survival rates also had the fastest malic acid degradations.

Example 7

Examination of New Dry Activation Composition Containing Commercially Available Freeze Dried *Oenococcus oeni* Strain A dry activation composition was produced as described in example 5 except for the bacteria strain where 15 g freeze dried product of the commercial culture Viniflora oenos from Chr. Hansen A/S, Denmark, was used. The product contain *Oenococcus oeni*, strain DSM 7008 and it is recommended by the producer for direct inoculation into wine at a concentration of 15 g per 2500 L wine.

The dry activation composition was re-hydrated by addition of water to a total of 1 L which resulted in a bacteria concentration of $1.2 \times 10^{10}$ CFU/ml. The activation solution was incubated at 23° C. and after 24 hours the number of bacteria in the activation solution was determined to be $1.1 \times 10^{10}$ CFU/mL indicating that no bacteria growth had occurred. After the 24 hours a sample of the activated bacteria solution was inoculated into 2.5 L Chardonnay wine from California with 12.5 vol % ethanol, pH 3.3 and with 20 ppm $SO_2$ added at crush. The inoculation resulted in an initial bacteria concentration of 5×10⁶ CFU/ml in the wine. 2.5 l of the wine was also inoculated directly with the freeze dried product according to instruction of the manufacture which also resulted in an initial bacteria concentration of 5×10⁶ CFU/ml. The wine was kept at 24° C. and followed by the determination of CFU/ml and malic acid concentration. FIG. 10 shows the results from the examination from which it can be calculated, that the survival rate measured day two was 40% in the wine inoculated directly with freeze dried bacteria while it was 100% in the wine inoculated with bacteria from the activation solution. In the later the bacteria also started to grow without a lag phase and the malolactic fermentation was completed within 16 days while it took 20 days in the wine inoculated directly with freeze dried bacteria.

The invention claimed is:

1. A method of producing a microbial organism capable of fermenting malic acid to lactic acid, wherein said method comprises the steps of
   i) Providing a microbial organism resistant to a pH below 5 and an ethanol concentration of at least 8%,
   ii) Subjecting said microbial organism to mutagenesis, thereby obtaining more than one different mutated microbial organism
   iii) Selecting a mutated microbial organisms capable of fermenting malic acid to lactic acid, wherein said selected mutated microbial organism when placed in a medium at an initial concentration in the range of 1×10⁶ to 5×10⁷ colony forming units per ml medium, said medium initially containing a predetermined amount of citric acid in the range of 100 to 1,000 mg/L, and a predetermined amount of malic acid in the range of 1,000 to 10,000 mg/L, is only capable of degrading at the most 50% of said citric acid within the period required for degradation of the malic acid within the medium to an amount not exceeding 30 mg/L, and wherein the selected mutated microbial organism is capable, under suitable growth conditions, of adaptation to, when said microbial organism in a frozen or freeze dried state is added directly into a fermented fruit juice:
      a) a survival rate which is at least 1% after two days at 23° C. in a fermented sterile fruit juice comprising at least 12 vol % ethanol; and/or
      b) a survival rate which is at least 70% after two days at 17° C. in a fermented sterile fruit juice comprising at least 13.9 vol % ethanol
   said organism being of a genus selected from the group consisting of *Lactobacillus*, *Pediococcus*, and *Oenococcus*.

2. The method according to claim 1, wherein said selected mutated microbial organism is resistant to pH 3.2.

3. The method according to claim 1, wherein said selected mutated microbial organism is resistant to an ethanol concentration of 13 vol %.

4. The method of claim 1, wherein the organism is of the genus *Oenococcus*.

5. The method of claim 1, wherein the organism is of the species *Oenococcus oeni*.

6. The method according to claim 1, wherein mutagenising comprises incubation in the presence of a chemical mutagenising agent.

7. The method according to claim 6, wherein said chemical mutagenising agent is selected from the group consisting of ethylmethanesulfonate, N-ethyl-N'-nitro-N-nitrosoguanidine, and 1-(2-hydroxyethyl)-1-nitrosourea.

8. An isolated and purified microbial organism, wherein said microbial organism is capable of fermenting malic acid to lactic acid, and wherein said microbial organism, when placed in a medium at an initial concentration in the range of 1×10⁶ to 5×10⁷ colony forming units per ml medium, said medium initially containing a predetermined amount of citric acid in the range of 100 to 1,000 mg/L, and a predetermined amount of malic acid in the range of 1,000 to 10,000 mg/L, is only capable of degrading at the most 50% of said citric acid within the period required for degradation of the malic acid within the medium to an amount not exceeding 30 mg/L,
and wherein the microbial organism is capable, under suitable growth conditions, of adaptation to, when said microbial organism in a frozen or freeze dried state is added directly into a fermented fruit juice:
   i) a survival rate which is at least 1% after two days at 23° C. in a fermented sterile fruit juice with a pH of less than 4 and comprising at least 12 vol % ethanol, and/or
   ii) a survival rate which is at least 70% after two days at 17° C. in a fermented sterile fruit juice with a pH of less than 4 comprising at least 13.9 vol % ethanol,
wherein said organism is obtained by the method of claim 1.

9. The microbial organism according to claim 8, wherein the organism has a survival rate which is at least 10% after two days at 23° C. in a wine prepared by yeasting a sterile grape fruit juice without added sulphite, said wine having an ethanol content of 12.0 vol %, pH 3.4, below 5 g/L residual sugar, 3.3 g/L of malic acid, and 450 mg/L of citric acid.

10. The microbial organism according to claim 8, wherein the organism has a survival rate which is in the range of 70% to 100% after two days at 18° C. in a wine prepared with 30 ppm SO₂ added before the alcoholic fermentation, said wine having an ethanol content of 13.8 vol %, pH 3.5, 1.3 g/L malic acid, and 340 mg/L of citric acid.

11. The microbial organism according to claim 8, wherein the organism has a survival rate which is at least 80% after two days at 17° C. in a wine prepared without SO₂ added, said wine having an ethanol content of 13.9 vol %, pH 3.6, 1.7 g/L malic acid, and 320 mg/L of citric acid.

12. The microbial organism according to claim 8, wherein said microbial organism when placed in a medium at an initial concentration in the range of 1×10⁶ to 5×10⁷ CFU/ml medium, said medium initially containing a predetermined amount of malic acid in the range of 1-10 g/L, is capable of degrading at least 90% of said malic acid.

13. The microbial organism according to claim 8, wherein said microbial organism reduces the citric acid content by less than 50% within 50 days, when added directly in a frozen or freeze dried state to a fermented fruit juice at a concentration of CFUs in the range of 1×10⁶ to 5×10⁷ per ml, wherein said fermented fruit juice is prepared by yeasting a sterile fruit juice without added sulphite resulting in a fermented fruit juice having an ethanol content of 12.0 vol %, pH 3.4, below 5 g/L residual sugar, 3.3 g/L of malic acid, and 450 mg/L of citric acid.

14. The microbial organism according to claim 8, wherein said organism is selected from the group consisting of strains deposited under the accession numbers DSM 15569, DSM 15570, and DSM 15571.

15. The organism according to claim 8, wherein the organism is capable of degrading at the most 50% of said citric acid within the period required for degradation of the malic acid within the medium to an amount not exceeding 15 mg/L.

16. The organism of claim 8, wherein the organism is of the genus *Oenococcus*.

17. The organism of claim 8, wherein the organism is of the species *Oenococcus oeni*.

18. A method of preferentially degrading malic acid over citric acid in a liquid composition comprising malic acid and citric acid, said method comprising the steps of
   i) Providing a liquid composition comprising malic acid and citric acid;
   ii) Providing a microbial organism according to claim 8, wherein said microbial organism has been frozen or freeze dried,
   iii) Adding said freeze dried or frozen microbial organism directly to said liquid composition
   iv) incubating said liquid composition and said microbial organism under conditions which allow degradation of at least 70% of the malic acid,
   v) thereby obtaining a final liquid composition comprising less than 30% of the initial malic acid and at least 20% of the initial citric acid.

19. The method according to claim 18, wherein the liquid composition is grape juice or fermented grape juice.

20. The method according to claim 18, wherein the liquid composition has a pH in the range of 2 to 5.

21. The method according to claim 18, wherein the liquid composition comprises in the range of 5 to 15 vol % ethanol.

22. The method according to claim 18, wherein the liquid composition comprises in the range of 1 to 10 g/L malic acid.

23. The method according to claim 18, wherein the liquid composition comprises in the range of 50 to 2000 mg/L citric acid.

24. The method according to claim 18, wherein the final liquid composition comprises at least 50% of the initial citric acid.

25. The method according to claim 18, wherein the finial liquid composition comprises less than 20% of the initial malic acid.

26. The method according to claim 18, wherein the microbial organism is added at a concentration of less than $5 \times 10^7$ CFU per ml of the liquid composition.

27. The method according to claim 19, wherein the fermented grape juice is selected from the group consisting of red wines, white wines and sparkling wines.

28. The method according to claim 18, wherein step iv) comprises incubation for a longer period of time than required for completion of malolactic fermentation.

29. A method of inducing malolactic fermentation during wine production, comprising the steps of
   i) Providing a grape juice or a fermented grape juice
   ii) Providing a microbial organism according to claim 8,
   iii) Incubating said grape juice or fermented grape juice with said microbial organism under conditions which allow degradation of malic acid,
   iv) thereby inducing malolactic fermentation.

30. The method according to claim 18, wherein said liquid composition is a grape juice or a fermented grape juice and said microbial organism in a frozen or freeze-dried state is added directly to said grape juice or a fermented grape juice.

31. The method according to claim 29, wherein the microbial organism is added at a concentration of less than $5 \times 10^7$ CFU per ml of the grape juice or a fermented grape juice.

32. The method according to claim 29, wherein the grape juice or a fermented grape juice has a pH in the range of 2 to 5.

33. The method according to claim 29, wherein the grape juice or a fermented grape juice comprises in the range of 5 to 15 vol % ethanol.

34. The method according to claim 29, wherein the grape juice or a fermented grape juice comprises in the range of 1 to 10 g/L malic acid.

35. The method according to claim 29, wherein the grape juice or a fermented grape juice comprises in the range of 50 to 2000 mg/L citric acid.

36. The method according to claim 29, wherein the wine is selected from the group consisting of red wines, white wines and sparkling wines.

37. A concentrate of microbial organisms comprising the microbial organism according to claim 8, wherein said concentrate has a content of colony forming units being in the range of $10^9$ to $10^{12}$ per g.

38. The concentrate according to claim 37, wherein said microbial organism has been propagated in an adaptation medium comprising at least 6% sugar.

39. The concentrate according to claim 38, wherein said adaptation medium comprises at least 3% glucose and at least 3% fructose.

40. The concentrate according to claim 38, wherein said microbial organism has been propagated in said adaptation medium for at least 12 hours.

41. A method of preparing a dried microbial organism capable of fermenting malic acid to lactic acid, which has reduced citric acid degrading activity and which is capable of survival after direct inoculation into fermented fruit juice, said method comprising the steps of
   i) Providing a microbial organism according to claim 8,
   ii) Providing an adaptation medium comprising at least 6% sugar
   iii) Propagating said microbial organism in said adaptation medium under conditions allowing growth of said microbial organism
   iv) Harvesting said microbial organism
   v) drying said microbial organism.

42. The method according to claim 41, wherein said adaptation medium comprises at least 3% glucose and at least 3% fructose.

43. The method according to claim 41, wherein said microbial organism is propagated in said adaptation medium for at least 12 hours.

44. An activation solution comprising
   i) A nitrogen source
   ii) In the range of 60 to 140 g sugar per L
   iii) In the range of $5 \times 10^8$ and $5 \times 10^{10}$ colony forming units per ml of a microbial organism according to claim 8,
   iv) a chemical compound with buffering capacity, wherein the solution has a pH in the range of 4 to 6.

45. The activation solution according to claim 44, wherein the microbial organism is selected from the group consisting of DSM 15569, DSM 15570, and DSM 15571.

46. The activation solution according to claim 44, wherein the sugar is selected from the group consisting of fructose and glucose.

47. The activation solution according to claim 46, wherein the glucose content of the solution is in the range of 30 g to 100 g glucose per liter solution.

48. The activation solution according to claim 46, wherein the fructose content of the solution is in the range of 30 g to 100 g fructose per liter solution.

49. The activation solution according to claim 44, wherein said chemical compound is selected from the group consisting of tartaric acid, malic acid, lactic acid, phosphate and citrate.

50. A dry activation composition, wherein in the range of 80 to 200 g of said dry activation composition comprises
   i. a nitrogen source ii. in the range of 60 to 140 g sugar iii. in the range of $5 \times 10^{11}$ and $5 \times 10^{13}$ colony forming units of a microbial organism according to claim 8, iv. a chemical compound with buffering capacity, wherein the chemical compound is capable of buffering a solution to a pH in the range of 4.0 to 6.0, wherein addition of water to said dry activation composition results in an activation solution.

51. The composition according to claim 50, wherein in the range of 110 to 150 g of said dry activation composition comprises in the range of 80 to 110 g sugar.

52. The composition according to claim 50, wherein the sugar is selected from the group consisting of fructose and glucose.

53. The composition according to claim 52, wherein the glucose concentration is 40 to 80 g/L and the fructose concentration is 40 to 80 g/L.

54. The composition according to claim 50, wherein the microbial organism is selected from the group consisting of DSM 15569, DSM 15570, and DSM 15571.

55. The composition according to claim 50, wherein the microbial organism after activation for more than 5 hours in the activation solution has a survival rate which is at least 3% after two days at 23° C. when inoculated into a fermented fruit juice having an ethanol content of at least 12.0 vol %.

56. The composition according to claim 55, wherein activation is in the range of 8 to 48 hours.

57. The composition according to claim 55, wherein activation is performed at a temperature in the range of 18° C. to 25° C.

58. The composition according to claim 55, wherein the survival rate is at least 33% after two days at 23° C. when inoculated into a fermented fruit juice prepared by yeasting a sterile grape fruit juice without added sulphite, said fermented fruit juice having an ethanol content of 12.0 vol %, pH 3.4, below 5 g/L residual sugar, 3.3 g/L of malic acid, and 450 mg/L of citric acid.

59. The composition according to claim 55, wherein the survival rate is at least 94% after two days at 23° C. when inoculated into a fermented fruit juice prepared by yeasting a sterile grape fruit juice without added sulphite, said fermented fruit juice having an ethanol content of 12.0 vol %, pH 3.4, below 5 g/L residual sugar, 3.3 g/L of malic acid, and 450 mg/L of citric acid.

60. The composition according to claim 50, wherein said chemical compound is selected from the group consisting of tartaric acid, malic acid, lactic acid, phosphate and citrate.

61. The composition according to claim 50, wherein said composition furthermore comprises a salt.

62. A method of inducing fermentation in a liquid composition comprising a fermentable compound comprising the steps of i. Providing a dry composition according to claim 50, wherein said microbial organism is capable of fermenting said fermentable compound ii. Adding water to said dry composition, thereby obtaining an activation solution iii. Incubating said activation solution for an activation time under activation conditions iv. Providing a liquid composition comprising said fermentable compound v. Inoculating said liquid composition with said activation solution vi. Thereby inducing fermentation in said liquid composition.

63. The method according to claim 62, wherein the liquid composition is a fruit juice or a fermented fruit juice.

64. The method according to claim 62, wherein the activation time is in the range of 8 to 48 hours.

65. The method according to claim 62, wherein activation conditions comprises incubation at a temperature in the range of 10° C. to 40° C.

66. The method according to claim 62, wherein the fermentable compound is malic acid.

67. The organism of claim 8, wherein said growth conditions suitable to adaptation to the survival rate of (i) and/or (ii) comprise propagation of said organism in an adaptation medium comprising at least 6% sugar.

68. The organism of claim 67, wherein said adaptation medium comprises at least 3% glucose and at least 3% fructose.

69. The organism of claim 67, wherein the organism is propagated in said adaptation medium for at least 12 hours.

70. The organism of claim 8, wherein the organism is selected from the group consisting of DSM15569, DSM15570, DSM15571, and mutants derived directly or indirectly therefrom by mutation and selection.

71. The organism of claim 8, wherein said method of obtaining the organism further comprises, after selection, the steps of:

i'. providing an adaptation medium comprising at least 6% sugar, and ii'. propagating said microbial organism in said adaptation medium under conditions allowing growth of said microbial organism.

* * * * *